(12) United States Patent
Wang et al.

(10) Patent No.: US 7,855,295 B2
(45) Date of Patent: Dec. 21, 2010

(54) TETRAHYDROCARBOLINE COMPOUNDS AS ANTICANCER AGENTS

(75) Inventors: Weibo Wang, Moraga, CA (US); Zhi-Jie Ni, Fremont, CA (US); Paul Barsanti, Pleasant Hill, CA (US); Sabina Pecchi, Oakland, CA (US); Yi Xia, Foster City, CA (US); Nathan Brammeier, Walnut Creek, CA (US); Megan C. Phillips, Walnut Creek, CA (US); Eliza Jazan, Richmond, CA (US); Kelly Wayman, San Rafael, CA (US); David Dibble, San Diego, CA (US); Jie-Kai Cheng, Shanghai (CN)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 855 days.

(21) Appl. No.: 11/042,474

(22) Filed: Jan. 24, 2005

(65) Prior Publication Data

US 2005/0215580 A1    Sep. 29, 2005

Related U.S. Application Data

(60) Provisional application No. 60/538,980, filed on Jan. 23, 2004.

(51) Int. Cl.
*A61K 31/437* (2006.01)
*C07D 487/04* (2006.01)
(52) U.S. Cl. .......................... 546/79; 546/80; 514/290
(58) Field of Classification Search .................. 546/79, 546/80; 514/292
See application file for complete search history.

(56) References Cited

U.S. PATENT DOCUMENTS

| | | | |
|---|---|---|---|
| 5,606,060 A | 2/1997 | Pommier et al. | 546/85 |
| 5,622,960 A | 4/1997 | Pommier et al. | 514/287 |
| 5,747,520 A | 5/1998 | Pommier et al. | 514/412 |
| 6,069,150 A | 5/2000 | Spinelli et al. | 514/312 |
| 2003/0040527 A1 | 2/2003 | Yeh et al. | |

FOREIGN PATENT DOCUMENTS

| | | |
|---|---|---|
| EP | 0 357 122 A2 | 3/1990 |
| EP | 0 300 541 | 3/1996 |
| EP | 1 070 716 | 1/2001 |
| JP | 3-287586 | 12/1991 |
| WO | WO 97/37658 | 10/1997 |
| WO | WO 01/87038 | 5/2001 |
| WO | WO 03/033496 | 4/2003 |

OTHER PUBLICATIONS

English abstract, DN 104:207248, JP 60246385 Yanagisawa Hiroaki et al 1985.*
Dorwald F. A. Side Reactions in Organic Synthesis, 2005, Wiley: VCH, Weinheim p. IX of Preface.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
English abstract DN 74:53396 Mukerdzhi et al . 1970.*
DN 112:77229 , Caplus English abstract CS 262100, 1989.*
Raju Mohan et al . 1996, Pictet-Spengler Reaction on Solid Support.*
The High Affinity Binding of [3H] Norharman ([3H]β-Carboline) to the Ethanol-Inducible Cytochrome P450 2E1 in Rat liver. Hans Rommelspacher et al 1999.*
Chou, Y.-L., et al., "Novel Serine-Based Linker for the Solid-Phase Synthesis of Organic Compunds," *Tetrahedron Letters* 39(8):757-760, 1998, cited by *CAplus* 1998:106945.
Deveau, A.M., et al., "The Synthesis of Amino-Acid Functionalized β-Carbolines as Topoisomerase II Inhibitors," *Bioorganic & Medicinal Chemistry Letters* 11:1251-1255, 2001.
Misztal, S., et al., "Structural and Spectral Properties of β-Carbolines. Part 4. Synthesis of the New Ring System: 9,10,15,15b-tetrahydroindolo[1', 2':4,3]pyrazino[2,1-a]carbolin-7(6H)-one," *Journal of the Chemical Society, Perkin Transactions 1: Organic and Bio-Organic Chemistry* 8:1871-1874, 1991, cited by *CAplus* 1991:583240.
Zhang and Cook, "A Successful Acid Promoted Asymmetric Picet-Spengler Reaction of $N_a$-BOC Protected Tryptophans. Effect of the BOC Group of Reactivity and Stereoselectivity" *Tetrahedron Letters* 36(39) : 6999-7002, 1995.
Cleaveland et al., "Identification of a Novel Inhibitor (NSC 665564) of Dihydroorotate Dehydrogenase with a Potency Equivalent of Brequinar" *Biochemical and Biophysical Research Communications* 223:654-659, 1996.
Connors et al., "Pictet-Spengler Synthesis of Tetrahydro-β-Carbolines Using Vinylsulfonylmethyl Resin" *Tetrahedron Letters* 43:6661-6663, 2002.
Horiguchi et al., "A Facile Synthesis of 1,1-Disubstituted 1,2,3,4-Tetrahydro-β-Carbolines . . . " *Heterocycles* 59(2)691-705, 2003.
Hotha et al., "HR22C16: A Potent Small-Molecule Probe for the Dynamics of Cell Division" *Angew. Chem. Int. Ed.* 42:2379-2382, 2003.

* cited by examiner

*Primary Examiner*—Rita J Desai
(74) *Attorney, Agent, or Firm*—Christensen O'Connor Johnson Kindness PLLC

(57) ABSTRACT

Tetrahydrocarboline compounds, pharmaceutically acceptable salts, and prodrugs thereof; compositions that include a pharmaceutically acceptable carrier and one or more of the tetrahydrocarboline compounds, either alone or in combination with at least one additional therapeutic agent. Methods of using the tetrahydrocarboline compounds, either alone or in combination with at least one additional therapeutic agent, in the prophylaxis or treatment of proliferative diseases.

11 Claims, 8 Drawing Sheets

TETRAHYDROCARBOLINE COMPOUNDS AS ANTICANCER AGENTS

CROSS-REFERENCE TO RELATED APPLICATION

This application claims the benefit of U.S. Provisional Patent Application No. 60/538,980, filed Jan. 23, 2004.

FIELD OF THE INVENTION

The present invention relates to new tetrahydrocarboline compounds, their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of proliferative diseases.

BACKGROUND OF THE INVENTION

Kinesins are motor proteins that use adenosine triphosphate (ATP) to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmatic reticulum. Several KRPs interact with the microtubules of the mitotic spindle or with the chromosomes directly, and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIFII) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., *Cell* 83:1159-1169, 1995). Mutations in bimC and cut7 genes, which are considered to be homologues of KSP, cause failure in centrosome separation in *Aspergillus Nidulans* (Enos, A. P., and N. R. Morris, *Cell* 60:1019-1027, 1990) and *Schizosaccharomyces Pombe* (Hagan, I., and M. Yanagida, *Nature* 347:563-566, 1990). Treatment of cells with either ATRA (all trans-retinoic acid), which reduces KSP expression on protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., *J. Biol. Chem.* 274, 18925-18931, 1999). Interestingly, the *Xenopus Laevis* Aurora-related protein kinase pEg2 was shown to associate and phosphorylate XlEg5 (Giet, R., et al., *J. Biol. Chem.* 274:15005-15013, 1999). Potential substrates of Aurora-related kinases are of particular interest for cancer drug development. For example, Aurora 1 and 2 kinases are overexpressed on protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., *Science* 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., *Biochemistry* 42:338-349, 2003; Kapoor, T. M., et al., *J. Cell Biol.* 150:975-988, 2000).

Recently, other KSP kinesin inhibitors have been described. WO 02/057244 and WO 02/056880 describe phenothiazine compounds and triphenylmethane compounds, respectively, for treating proliferative diseases. WO 02/078639 describes cyano-substituted dihydropyrimidine compounds for treating proliferative diseases. U.S. Pat. No. 6,472,521 describes oligonucleotides and oligonucleotide derivatives for inhibiting human KSP expression.

WO 01/98278, WO 01/30768, and WO 03/039460 describe quinazolinone compounds that are useful in treating cellular proliferative diseases associated with KSP activity. The compounds described in these references are 2-(2-aminomethyl)quinazolinone derivatives. The quinazolinone compounds described in WO 01/98278 and WO 01/30768 have 2-aminomethyl substituents that are either amine, amide, or sulfonamide substituents. The quinazolinone compounds described in WO 03/039460 have the amino group of the 2-aminomethyl substituent incorporated into a 5-12 membered nitrogen-containing heterocycle.

WO 03/050064 describes thienopyrimidinone compounds that are useful for treating cellular proliferative disease, for treating disorders associated with KSP activity, and for inhibiting KSP.

WO 03/103575 describes heterocyclic-fused pyrimidinone derivatives that are inhibitors of the mitotic KSP and that are useful in the treatment of cellular proliferative diseases.

Tetrahydrocarbolines have been used as topoisomerase II inhibitors, protein tyrosine phosphatases (PTPases) inhibitors, and phosphodiesterase inhibitors. U.S. Pat. No. 5,606,060 describes azatoxin and derivatives as antitumor drugs that are topoisomerase II inhibitors. WO 03/033496 describes beta-carboline derivatives as anticancer drugs that are protein tyrosine phosphatases inhibitors. U.S. Pat. No. 6,069,150 describes beta-carboline derivatives bearing at least a free or esterified carboxylic group on the piperidine ring that have antimetastatic properties. WO 01/87038 describes beta-carboline derivatives for the treatment of diseases and conditions related to phosphodiesterase inhibitors (PDE) such as male erectile dysfunction.

SUMMARY OF THE INVENTION

In one aspect of the present invention, new tetrahydrocarboline compounds, their pharmaceutically acceptable salts, and prodrugs thereof are provided. The tetrahydrocarboline compounds, pharmaceutically acceptable salts, and prodrugs are KSP inhibitors and are useful in the treating cellular proliferation diseases.

In one embodiment, the tetrahydrocarboline compounds have the formula (I):

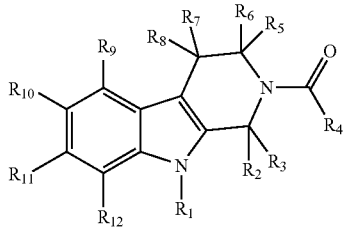

(I)

or a stereoisomer, tautomer, pharmaceutically acceptable salt, ester, or prodrug thereof, wherein, $R_1$ is selected from the group consisting of
  (1) hydrogen, and
  (2) substituted or unsubstituted $C_1$-$C_6$ alkyl;

$R_2$ is selected from the group consisting of
  (1) substituted or unsubstituted $C_5$-$C_8$ cycloalkyl,
  (2) substituted or unsubstituted aryl,
  (3) substituted or unsubstituted heteroaryl,
  (4) substituted or unsubstituted heterocyclyl, and
  (5) $CONR_{2a}R_{2b}$,
    wherein $R_{2a}$ and $R_{2b}$ are selected from the group consisting of
      (a) hydrogen
      (b) substituted or unsubstituted $C_3$-$C_8$ cycloalkyl,
      (c) substituted or unsubstituted aryl,
      (d) substituted or unsubstituted heteroaryl, and
      (e) substituted or unsubstituted heterocyclyl;

$R_3$ is selected from the group consisting of
  (1) hydrogen, and
  (2) substituted or unsubstituted alkyl;

$R_4$ is selected from the group consisting of
  (1) substituted or unsubstituted alkyl, wherein substituted alkyl is not a halomethyl,
  (2) substituted or unsubstituted cycloalkyl, and
  (3) substituted or unsubstituted heterocyclyl;

$R_5$ is selected from the group consisting of
  (1) hydrogen,
  (2) $CO_2R_{5a}$, and
  (3) $CONR_{5b}R_{5c}$,
    wherein $R_{5a}$, $R_{5b}$, and $R_{5c}$ are selected from the group consisting of
      (a) substituted or unsubstituted alkyl,
      (b) substituted or unsubstituted aryl,
      (c) substituted or unsubstituted heteroaryl, and
      (d) substituted or unsubstituted heterocyclyl;

$R_6$ is hydrogen;
$R_7$ is hydrogen or hydroxy;
$R_8$ is hydrogen, or
$R_7$ and $R_8$ taken together with the carbon atom to which $R_7$ and $R_8$ are attached form a carbonyl;

$R_{10}$ is selected from the group consisting of
  (1) substituted or unsubstituted alkyl,
  (2) substituted or unsubstituted aryl,
  (3) substituted or unsubstituted heteroaryl,
  (4) substituted or unsubstituted heterocyclyl,
  (5) halogen,
  (6) $OR_{10a}$,
  (7) $CO_2R_{10a}$,
  (8) $NR_{10a}R_{11a}$,
  (9) $CONR_{10a}R_{11a}$,
  (10) $SO_2NR_{10a}R_{11a}$, wherein $R_{10a}$ and $R_{11a}$ are selected from the group consisting of
  (a) hydrogen,
  (b) substituted or unsubstituted alkyl, and
  (c) substituted or unsubstituted aryl; and $R_9$, $R_{11}$, and $R_{12}$ are selected from the group consisting of
  (1) hydrogen,
  (2) substituted or unsubstituted alkyl,
  (3) substituted or unsubstituted aryl,
  (4) halogen, and
  (5) $OR_{9a}$,
    wherein $R_{9a}$ is selected from the group consisting of
      (a) hydrogen,
      (b) substituted or unsubstituted alkyl, and
      (c) substituted or unsubstituted aryl, with the proviso that when $R_1$ is hydrogen, $R_2$ is phenyl, and $R_{10}$ is bromo, $R_4$ is not methyl, with the proviso that when $R_1$ is hydrogen, $R_2$ is nitrophenyl or chloro nitrophenyl, and $R_{10}$ is methoxy, $R_4$ is not adamantyl, with the proviso that when $R_1$ is hydrogen, $R_2$ is phenyl, $R_4$ is methyl, and $R_{10}$ is hydroxy, $R_5$ is not $CO_2CH_3$, and with the proviso that when $R_4$ is methyl or hydroxymethyl, $R_2$ is not phenyl, 4-hydroxyphenyl, 3-methoxy-4-hydroxyphenyl, or 3,5-dimethoxy-4-hydroxyphenyl.

In another aspect, the present invention provides methods for treating proliferative diseases in a human or animal subject in need of such treatment comprising administering to said subject an amount of a compound of formula (I) effective to reduce or prevent cellular proliferation in the subject.

In another aspect, the present invention provides methods for treating proliferative diseases in a human or animal subject in need of such treatment, comprising administering to said subject an amount of a compound of formula (I) effective to reduce prevent cellular proliferation in the subject in combination with at least one additional agent for the treatment of cancer.

In other aspects, the present invention provides therapeutic compositions, comprising at least one compound of formula (I) in combination with one or more additional agents for the treatment of cancer, as are commonly employed in cancer therapy.

The compounds of the invention are useful in the treatment of cancers, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-hodgkin lymphoma; melanoma; and villous colon adenoma.

The invention further provides compositions, kits, methods of use, and methods of manufacture as described in the detailed description of the invention.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
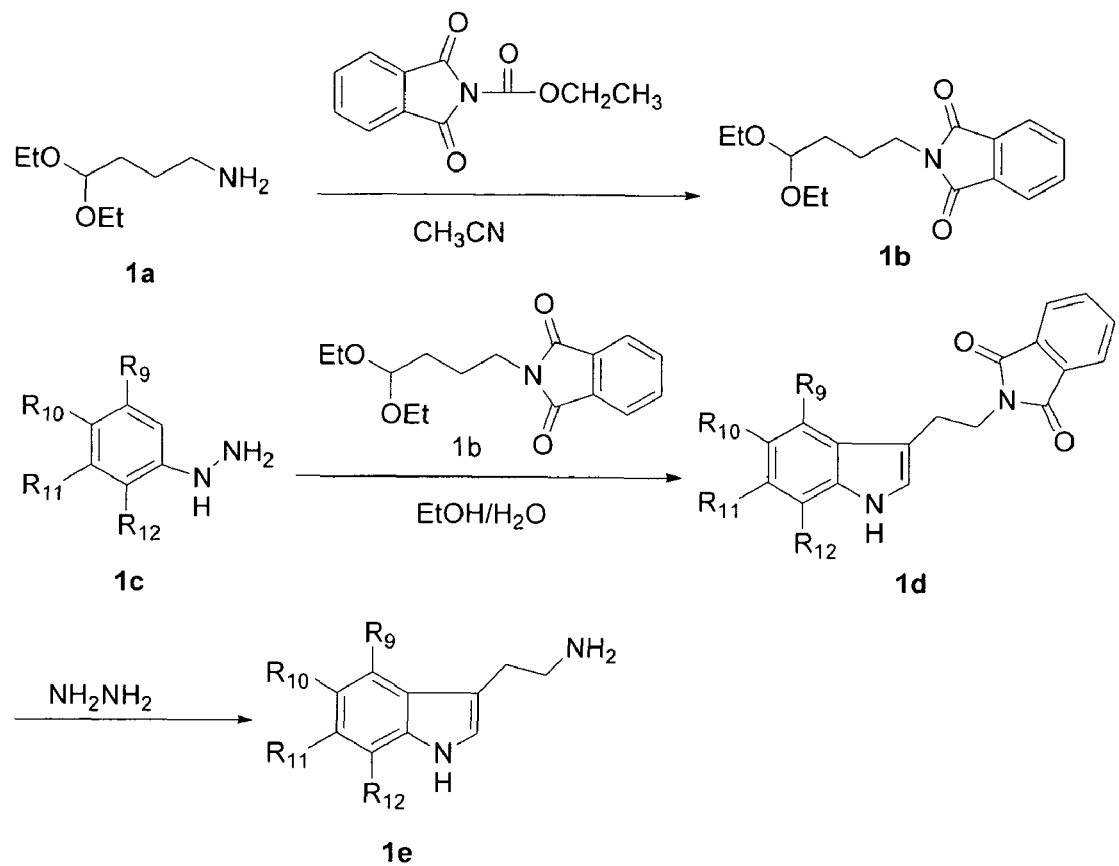
FIG. 1 is a synthetic scheme illustrating the preparation of representative substituted tryptamine compounds useful in synthesizing the tetrahydrocarboline compounds of the invention.

In one aspect of the present invention, new tetrahydrocarboline compounds, their pharmaceutically acceptable salts, and prodrugs thereof are provided. The tetrahydrocarboline compounds, pharmaceutically acceptable salts, and prodrugs are KSP inhibitors and are useful in the treating cellular proliferation diseases.

In one embodiment, the tetrahydrocarboline compounds of the invention have the formula (I):

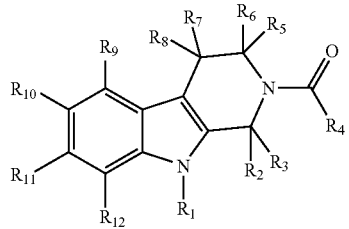

(I)

or a stereoisomer, tautomer, pharmaceutically acceptable salt, ester, or prodrug thereof, wherein, $R_1$ is selected from the group consisting of
  (1) hydrogen, and
  (2) substituted or unsubstituted $C_1$-$C_6$ alkyl;

$R_2$ is selected from the group consisting of
  (1) substituted or unsubstituted $C_5$-$C_8$ cycloalkyl,
  (2) substituted or unsubstituted aryl,
  (3) substituted or unsubstituted heteroaryl,
  (4) substituted or unsubstituted heterocyclyl, and
  (5) $CONR_{2a}R_{2b}$,
  wherein $R_{2a}$ and $R_{2b}$ are selected from the group consisting of
    (a) hydrogen
    (b) substituted or unsubstituted $C_3$-$C_8$ cycloalkyl,
    (c) substituted or unsubstituted aryl,
    (d) substituted or unsubstituted heteroaryl, and
    (e) substituted or unsubstituted heterocyclyl;

$R_3$ is selected from the group consisting of
  (1) hydrogen, and
  (2) substituted or unsubstituted alkyl;

$R_4$ is selected from the group consisting of
  (1) substituted or unsubstituted alkyl, wherein substituted alkyl is not a halomethyl,
  (2) substituted or unsubstituted cycloalkyl, and
  (3) substituted or unsubstituted heterocyclyl;

$R_5$ is selected from the group consisting of
  (1) hydrogen,
  (2) $CO_2R_{5a}$, and
  (3) $CONR_{5b}R_{5c}$,
  wherein $R_{5a}$, $R_{5b}$, and $R_{5c}$ are selected from the group consisting of
    (a) substituted or unsubstituted alkyl,
    (b) substituted or unsubstituted aryl,
    (c) substituted or unsubstituted heteroaryl, and
    (d) substituted or unsubstituted heterocyclyl;

$R_6$ is hydrogen;

$R_7$ is hydrogen or hydroxy;

$R_8$ is hydrogen, or $R_7$ and $R_8$ taken together with the carbon atom to which $R_7$ and $R_8$ are attached form a carbonyl;

$R_{10}$ is selected from the group consisting of
  (1) substituted or unsubstituted alkyl,
  (2) substituted or unsubstituted aryl,
  (3) substituted or unsubstituted heteroaryl,
  (4) substituted or unsubstituted heterocyclyl,
  (5) halogen,
  (6) $OR_{10a}$,
  (7) $CO_2R_{10a}$,
  (8) $NR_{10a}R_{11a}$,
  (9) $CONR_{10a}R_{11a}$,
  (10) $SO_2NR_{10a}R_{11a}$,
  wherein $R_{10a}$ and $R_{11a}$ are selected from the group consisting of
    (a) hydrogen,
    (b) substituted or unsubstituted alkyl, and
    (c) substituted or unsubstituted aryl; and $R_9$, $R_{11}$, and $R_{12}$ are selected from the group consisting of
  (1) hydrogen,
  (2) substituted or unsubstituted alkyl,
  (3) substituted or unsubstituted aryl,
  (4) halogen, and
  (5) $OR_{9a}$,
  wherein $R_{9a}$ is selected from the group consisting of
    (a) hydrogen,
    (b) substituted or unsubstituted alkyl, and
    (c) substituted or unsubstituted aryl, with the proviso that when $R_1$ is hydrogen, $R_2$ is phenyl, and $R_{10}$ is bromo, $R_4$ is not methyl, with the proviso that when $R_1$ is hydrogen, $R_2$ is nitrophenyl or chloro nitrophenyl, and $R_{10}$ is methoxy, $R_4$ is not adamantyl, with the proviso that when $R_1$ is hydrogen, $R_2$ is phenyl, $R_4$ is methyl, and $R_{10}$ is hydroxy, $R_5$ is not $CO_2CH_3$, and with the proviso that when $R_4$ is methyl or hydroxymethyl, $R_2$ is not phenyl, 4-hydroxyphenyl, 3-methoxy-4-hydroxyphenyl, or 3,5-dimethoxy-4-hydroxyphenyl.

In another embodiment, the tetrahydrocarboline compounds of the invention have formula (I) above, or a stereoisomer, tautomer, pharmaceutically acceptable salt, ester, or prodrug thereof, wherein, $R_1$ is selected from the group consisting of
  (1) hydrogen, and
  (2) substituted or unsubstituted $C_1$-$C_6$ alkyl;

$R_2$ is selected from the group consisting of
  (1) substituted or unsubstituted aryl, and
  (2) substituted or unsubstituted heteroaryl;

$R_3$ is selected from the group consisting of
   (1) hydrogen, and
   (2) substituted or unsubstituted alkyl;
$R_4$ is a nitrogen-containing substituent;
$R_5$ is selected from the group consisting of
   (1) hydrogen,
   (2) $CO_2R_{5a}$, and
   (3) $CONR_{5b}R_{5c}$,
      wherein $R_{5a}$, $R_{5b}$, and $R_{5c}$ are selected from the group consisting of
         (a) substituted or unsubstituted alkyl,
         (b) substituted or unsubstituted aryl,
         (c) substituted or unsubstituted heteroaryl, and
         (d) substituted or unsubstituted heterocyclyl;
$R_6$ is hydrogen;
$R_7$ is hydrogen or hydroxy;
$R_8$ is hydrogen, or
$R_7$ and $R_8$ taken together with the carbon atom to which $R_7$ and $R_8$ are attached form a carbonyl;
$R_{10}$ is selected from the group consisting of
   (1) substituted or unsubstituted alkyl,
   (2) substituted or unsubstituted aryl,
   (3) substituted or unsubstituted heteroaryl,
   (4) substituted or unsubstituted heterocyclyl,
   (5) halogen,
   (6) $OR_{10a}$,
   (7) $CO_2R_{10a}$,
   (8) $NR_{10a}R_{11a}$,
   (9) $CONR_{10a}R_{11a}$,
   (10) $SO_2NR_{10a}R_{11a}$,
      wherein $R_{10a}$ and $R_{11a}$ are selected from the group consisting of
         (a) hydrogen,
         (b) substituted or unsubstituted alkyl, and
         (c) substituted or unsubstituted aryl, and
$R_9$, $R_{11}$, and $R_{12}$ are selected from the group consisting of
   (1) hydrogen,
   (2) substituted or unsubstituted alkyl,
   (3) substituted or unsubstituted aryl,
   (4) halogen, and
   (5) $OR_{9a}$,
      wherein $R_{9a}$ is selected from the group consisting of
         (a) hydrogen,
         (b) substituted or unsubstituted alkyl, and
         (c) substituted or unsubstituted aryl.

The following embodiments relate to the tetrahydrocarboline compounds having formula (I) described above.

In one embodiment, $R_1$ is hydrogen.

In one embodiment, $R_2$ is phenyl or substituted phenyl. The phenyl group may be substituted with one or more substituents including, for example, alkyl, alkoxy, amino, carboxy, halogen, hydroxy, thioalkyl, and alkylsulfonate groups. In one embodiment, $R_2$ is 3-hydroxyphenyl.

In one embodiment, $R_3$ is hydrogen.

In one embodiment, $R_2$ is a phenyl or substituted phenyl, and $R_3$ is hydrogen.

In one embodiment, $R_4$ is a nitrogen-containing substituent, for example, an alkyl group substituted with a nitrogen-containing group. Representative nitrogen-containing groups include amino groups (e.g., primary, secondary, and tertiary amino groups) and cyclic amino groups (e.g., azetidinyl, pyrrolidinyl, piperidinyl, piperizinyl, and morpholinyl); amide groups (e.g., —C(=O)—$NR_2$, where R is hydrogen or alkyl; and —NH—C(=O)—R, where R is alkyl or aryl, such as methyl, trifluoromethyl, and phenyl); carbamate groups (e.g., methyl, ethyl, isopropyl, or t-butyl carbamate groups); and sulfonamide groups (e.g., —$NHSO_2R$, where R is alkyl or aryl, such as methyl and phenyl). In one embodiment, $R_4$ is aminoalkyl, for example, aminomethyl, 2-aminoethyl, 3-aminopropyl.

In one embodiment, $R_5$, $R_6$, $R_7$, and $R_8$ are hydrogen.

In one embodiment, $R_9$, $R_{11}$, and $R_{12}$ are hydrogen.

In another embodiment, $R_{10}$ is selected from alkyl (e.g., methyl, ethyl, isopropyl), alkoxy (e.g., methoxy, trifluoromethoxy), aryl (e.g., phenyl, methoxyphenyl, tolyl) halo (e.g., fluoro, chloro, bromo), and hydroxy.

For the compounds of formulas (I), representative substituted alkyl groups include arylalkyl, heteroarylalkyl, heterocyclyalkyl, aminoalkyl, alkylaminoalkyl, dialkylaminoalkyl, and sulfonamidoalkyl groups. Representative substituted aryl groups include sulfonamidoaryl groups. Representative substituted heteroaryl groups include alkylheteroaryl groups.

The synthesis of representative tetrahydrocarboline compounds are described in Examples 2-11. Representative tetrahydrocarboline compounds that were prepared are shown in Table 1 in Example 12.

In other aspects, the present invention provides methods for manufacture of tetrahydrocarboline compounds. Methods of making representative compounds of the invention are described in Examples 2-11. It is further contemplated that, in addition to the compounds of formula (I), intermediates, and their corresponding methods of syntheses are included within the scope of the invention. Representative compounds of the invention are illustrated in Table 1 in Example 12.

In other aspects, the present invention provides compositions that include the KSP inhibitors described herein, and methods that utilize the KSP inhibitors described herein.

In one aspect, the present invention provides pharmaceutical compositions comprising at least one tetrahydrocarboline compound (e.g., a compound of formula (I)) together with a pharmaceutically acceptable carrier suitable for administration to a human or animal subject, either alone or together with other anticancer agents.

A number of suitable anticancer agents to be used as combination therapeutics are contemplated for use in the compositions and methods of the present invention. Suitable anticancer agents to be used in combination with the compounds of the invention include agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons [e.g., IFN-a] and interleukins [e.g., IL-2]); adoptive immunotherapy agents; hematopoietic growth factors; agents that induce tumor cell differentiation (e.g., all-trans-retinoic acid); gene therapy reagents; antisense therapy reagents and nucleotides; tumor vaccines; inhibitors of angiogenesis, and the like. Numerous other examples of chemotherapeutic compounds and anticancer therapies suitable for coadministration with the tetrahydrocarboline compounds of the invention are known to those skilled in the art.

In certain embodiments, anticancer agents to be used in combination with tetrahydrocarboline compounds of the invention comprise agents that induce or stimulate apoptosis. Agents that induce apoptosis include, but are not limited to, radiation; kinase inhibitors (e.g., Epidermal Growth Factor Receptor [EGFR] kinase inhibitor, Vascular Endothelial Growth Factor Receptor [VEGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571 [Gleevec or Glivec]); antisense molecules; antibodies [e.g., Herceptin and Rituxan]; anti-estrogens [e.g., raloxifene and tamoxifen]; anti-androgens [e.g., flutamide, bicalutamide, finasteride, amino-glutethamide, ketoconazole, and corticosteroids]; cyclooxygenase 2 (COX-2) inhibitors [e.g., Celecoxib, meloxicam, NS-398, and non-steroidal anti-inflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, TAXOTERE or TAXOL]; cellular signaling molecules; ceramides and cytokines; and staurosparine; and the like.

In other aspects, the invention provides methods for using the compounds described herein. For example, the compounds described herein can be used in the treatment of cancer. The compounds described herein can also be used in the manufacture of a medicament for the treatment of cancer.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of an tetrahydrocarboline compound (e.g., a compound of formula (I)), either alone or in combination with other anticancer agents.

In another embodiment, the present invention provides methods for treating a cellular proliferative disease in a human or animal subject in need of such treatment comprising, administering to said subject an amount of an tetrahydrocarboline compound (e.g., a compound of formula (I)) effective to reduce or prevent cellular proliferation or tumor growth in the subject.

In another embodiment, the present invention provides methods for treating a cellular proliferative disease in a human or animal subject in need of such treatment comprising administering to said subject an amount of an tetrahydrocarboline compound (e.g., a compound of formula (I)) effective to reduce or prevent cellular proliferation in the subject in combination with at least one additional agent for the treatment of cancer.

The present invention provides compounds that are inhibitors of KSP. The inhibitors are useful in pharmaceutical compositions for human or veterinary use where inhibition of KSP is indicated, e.g., in the treatment of cellular proliferative diseases such as tumor and/or cancerous cell growth mediated by KSP. In particular, the compounds are useful in the treatment of human or animal (e.g., murine) cancers, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-hodgkin lymphoma; melanoma; and villous colon adenoma.

In another embodiment, the invention provides methods of treating an KSP mediated disorder. In one method, an effective amount of an tetrahydrocarboline compound is administered to a patient (e.g., a human or animal subject) in need thereof to mediate (or modulate) KSP activity.

A representative assay for determining KSP inhibitory activity is described in Example 13.

In some embodiments of the method of inhibiting KSP using a tetrahydrocarboline compound of the invention, the $IC_{50}$ value of the compound is less than or equal to 1 mM with respect to KSP. In other such embodiments, the $IC_{50}$ value is less than or equal to 100 μM, is less than or equal to 25 μM, is less than or equal to 10 μM, is less than or equal to 1 μM, is less than or equal to 0.1 μM, is less than or equal to 0.050 μM, or is less than or equal to 0.010 μM.

In some embodiments of the method of inhibiting KSP using a tetrahydrocarboline compound of the invention, the $IC_{50}$ value of the compound is between 1 nM to 10 nM. In other such embodiments, the $IC_{50}$ value is between 10 nM to 50 nM, between 50 nM to 100 nM, between 100 nM to 1 μM, between 1 μM to 25 μM, or is between 25 μM to 100 μM.

The following definitions are provided to better understand the invention.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$) (CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH (CH$_2$CH$_3$)$_2$, —CH$_2$C(CH$_3$)$_3$, —CH$_2$C(CH$_2$CH$_3$)$_3$, —CH (CH$_3$)—CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$) CH$_2$CH(CH$_3$)$_2$, —CH(CH$_3$)CH(CH$_3$)CH(CH$_3$)$_2$, —CH (CH$_2$CH$_3$)CH(CH$_3$)CH(CH$_3$)(CH$_2$CH$_3$), and others. Thus the phrase "alkyl groups" includes primary alkyl groups, secondary alkyl groups, and tertiary alkyl groups. Preferred alkyl groups include straight and branched chain alkyl groups having 1 to 12 carbon atoms.

"Alkylene" refers to the same residues as noted above for "alkyl," but having two points of attachment. Exemplary alkylene groups include ethylene (—CH$_2$CH$_2$—), propylene (—CH$_2$CH$_2$CH$_2$—), dimethylpropylene (—CH$_2$C(CH$_3$)$_2$ CH$_2$—), and cyclohexylpropylene (—CH$_2$CH$_2$CH (C$_6$H$_{13}$)—).

"Alkenyl" refers to straight chain, branched, or cyclic radicals having one or more carbon-carbon double bonds and from 2 to about 20 carbon atoms. Preferred alkenyl groups include straight chain and branched alkenyl groups and cyclic alkenyl groups having 2 to 12 carbon atoms.

"Alkynyl" refers to straight chain, branched, or cyclic radicals having one or more carbon-carbon triple bonds and from 2 to about 20 carbon atoms. Preferred alkynyl groups include straight chain and branched alkynyl groups having 2 to 12 carbon atoms.

Alkyl, alkenyl, and alkynyl groups may be substituted. "Substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heteroaryl, heterocyclyl, or cycloalkyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —$(CH_2)_3NH_2$, —$(CH_2)_3NH(CH_3)$, —$(CH_2)_3NH(CH_3)_2$, —$CH_2C(=CH_2)$ $CH_2NH_2$, —$CH_2C(=O)CH_2NH_2$, —$CH_2S(=O)_2CH_3$, —$CH_2OCH_2NH_2$, —$CO_2H$. Examples of substituents of substituted alkyl are: —$CH_3$, —$C_2H_5$, —$CH_2OH$, —OH, —$OCH_3$, —$OC_2H_5$, —$OCF_3$, —$OC(=O)CH_3$, —$OC(=O)$ $NH_2$, —$OC(=O)N(CH_3)_2$, —CN, —$NO_2$, —$C(=O)CH_3$, —$CO_2H$, —$CO_2CH_3$, —$CONH_2$, —$NH_2$, —$N(CH_3)_2$, —$NHSO_2CH_3$, —$NHCOCH_3$, —$NHC(=O)OCH_3$, —$NHSO_2CH_3$, —$SO_2CH_3$, —$SO_2NH_2$, Halo.

"Substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

"Substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkoxy" refers to RO— wherein R is alkyl. Representative examples of alkoxy groups include methoxy, ethoxy, t-butoxy, trifluoromethoxy, and the like.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

"Amino" refers herein to the group —$NH_2$. The term "alkylamino" refers herein to the group —NRR' where R is alkyl and R' is hydrogen or alkyl. The term "arylamino" refers herein to the group —NRR' where R is aryl and R' is hydrogen, alkyl, or aryl. The term "aralkylamino" refers herein to the group —NRR' where R is aralkyl and R' is hydrogen, alkyl, aryl, or aralkyl.

"Alkoxyalkyl" refers to the group -$alk_1$-O-$alk_2$ where $alk_1$ is alkyl or alkenyl, and $alk_2$ is alkyl or alkenyl. The term "aryloxyalkyl" refers to the group -alkyl O-aryl. The term "aralkoxyalkyl" refers to the group -alkylenyl-O-aralkyl.

"Alkoxyalkylamino" refers herein to the group —NR-(alkoxyalkyl), where R is typically hydrogen, aralkyl, or alkyl.

"Aminocarbonyl" refers herein to the group —C(O)—$NH_2$. "Substituted aminocarbonyl" refers herein to the group —C(O)—NRR' where R is alkyl and R' is hydrogen or alkyl. The term "arylaminocarbonyl" refers herein to the group —C(O)—NRR' where R is aryl and R' is hydrogen, alkyl or aryl. "Aralkylaminocarbonyl" refers herein to the group —C(O)—NRR' where R is aralkyl and R' is hydrogen, alkyl, aryl, or aralkyl.

"Aminosulfonyl" refers herein to the group —$S(O)_2$—$NH_2$. "Substituted aminosulfonyl" refers herein to the group —$S(O)_2$—NRR' where R is alkyl and R' is hydrogen or alkyl. The term "aralkylaminosulfonlyaryl" refers herein to the group -aryl-$S(O)_2$—NH-aralkyl.

"Carbonyl" refers to the divalent group —C(O)—.

"Carbonyloxy" refers generally to the group —C(O)—O. Such groups include esters, —C(O)—O—R, where R is alkyl, cycloalkyl, aryl, or aralkyl. The term "carbonyloxycycloalkyl" refers generally herein to both a "carbonyloxycarbocycloalkyl" and a "carbonyloxyheterocycloalkyl," i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl.

"Sulfonyl" refers herein to the group —$SO_2$—. "Alkylsulfonyl" refers to a substituted sulfonyl of the structure —$SO_2R$— in which R is alkyl. Alkylsulfonyl groups employed in compounds of the present invention are typically alkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —$SO_2$-aryl. The term "aralkylsulfonyl" refers herein to the group —$SO_2$-aralkyl. The term "sulfonamido" refers herein to —$SO_2NH_2$.

"Carbonylamino" refers to the divalent group —NH—C(O)— in which the hydrogen atom of the amide nitrogen of the carbonylamino group can be replaced alkyl, aryl, or aralkyl group. Such groups include moieties such as carbamate esters (—NH—C(O)—O—R) and amides —NH—C(O)—R, where R is a straight or branched chain alkyl, cycloalkyl, or aryl or aralkyl. The term "alkylcarbonylamino" refers to alkylcarbonylamino where R is alkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is aralkyl.

"Guanidino" or "guanidyl" refers to moieties derived from guanidine, $H_2N$—C(=NH)—$NH_2$. Such moieties include those bonded at the nitrogen atom carrying the formal double bond (the "2"-position of the guanidine, e.g., diaminomethyleneamino, $(H_2N)_2C$=NH—)) and those bonded at either of the nitrogen atoms carrying a formal single bond (the "1-" and/or "3"-positions of the guandine, e.g., $H_2N$—C(=NH)—NH—)). The hydrogen atoms at any of the nitrogens can be replaced with a suitable substituent, such as alkyl, aryl, or aralkyl.

"Amidino" refers to the moieties R—C(=N)—NR'— (the radical being at the "$N^1$" nitrogen) and R(NR')C=N— (the radical being at the "$N^2$" nitrogen), where R and R' can be hydrogen, alkyl, aryl, or aralkyl.

"Cycloalkyl" refers to a mono- or polycyclic, heterocyclic or carbocyclic alkyl substituent. Representative cycloalkyl groups include cyclopropyl, cyclobutyl, cyclopentyl, cyclohexyl, cycloheptyl, and cyclooctyl and such rings substituted with straight and branched chain alkyl groups as defined above. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl, and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Substituted heterocycle," "heterocyclic group," "heterocycle," or "heterocyclyl," as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom may be optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piper-azinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, and benzothienyl.

Heterocyclic moieties can be unsubstituted or monosubstituted or disubstituted with various substituents independently selected from hydroxy, halo, oxo (C=O), alkylimino (RN=, wherein R is alkyl or alkoxy group), amino, alkylamino, dialkylamino, acylaminoalkyl, alkoxy, thioalkoxy, polyalkoxy, alkyl, cycloalkyl or haloalkyl.

The heterocyclic groups may be attached at various positions as will be apparent to those having skill in the organic and medicinal chemistry arts in conjunction with the disclosure herein.

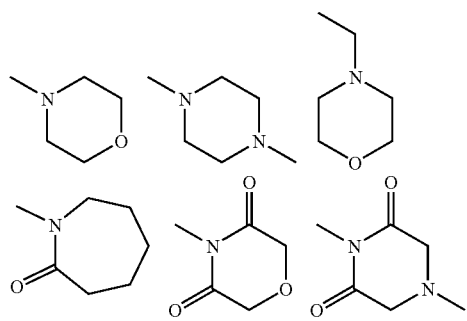

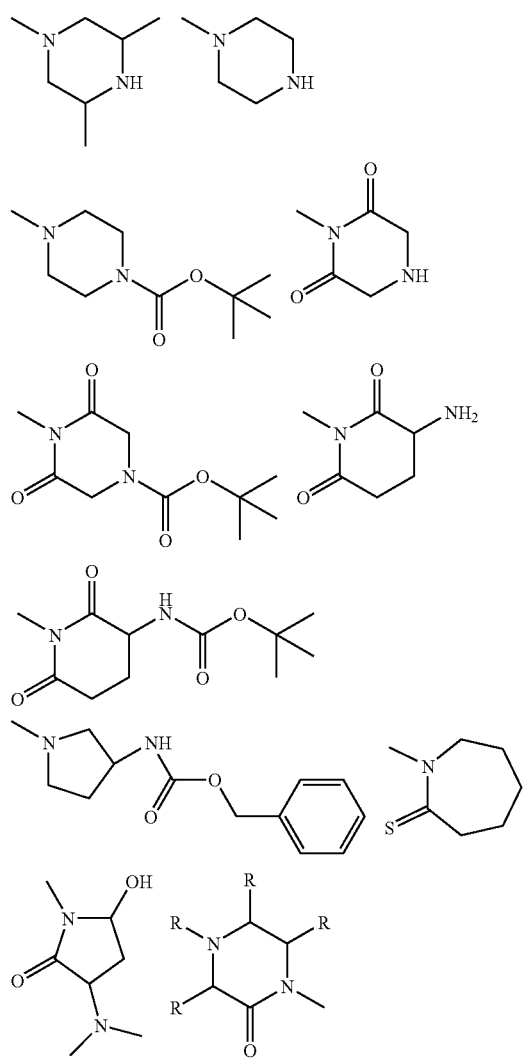

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

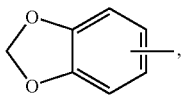

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

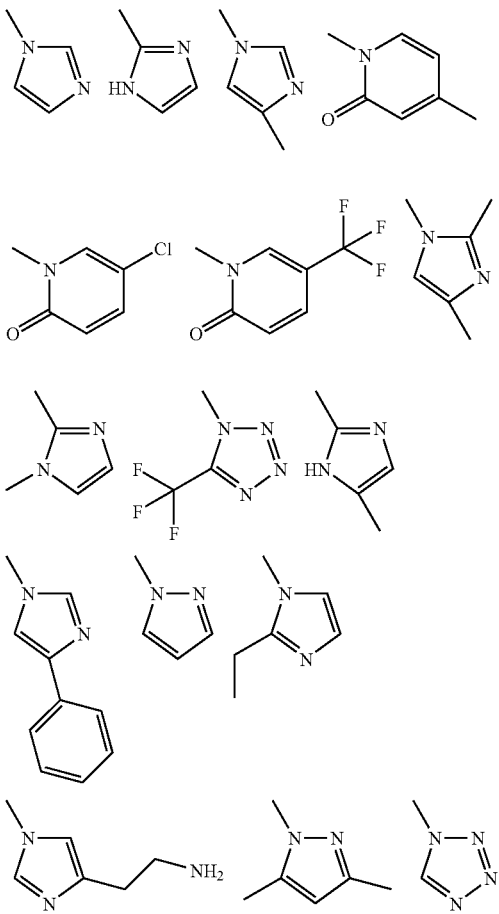

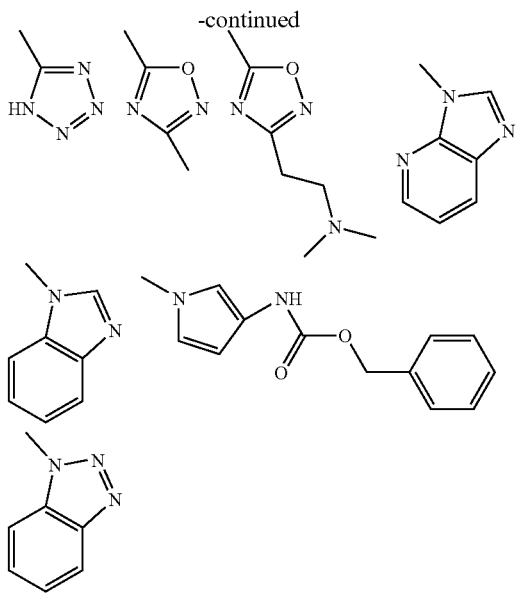

Representative heteroaryls include, for example, imidazolyl, pyridyl, thiazolyl, triazolyl benzimidazolyl, benzothiazolyl, and benzoxazolyl.

"Biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)-phenyl]acetamide, 1,4-diphenylbenzene, N-[4-(2-phenylethynyl)phenyl]-2-[benzyl-amino]-acetamide, 2-amino-N-[4-(2-phenylethynyl) phenyl]propanamide, 2-amino-N-[4-(2-phenyl-ethynyl) phenyl]acetamide, 2-(cyclopropylamino)-N-[4-(2-phenylethynyl)-phenyl]-acetamide, 2-(ethylamino)-N-[4-(2-phenylethynyl)phenyl]acetamide, 2-[(2-methyl-propyl) amino]-N-[4-(2-phenylethynyl)phenyl]acetamide, 5-phenyl-2H-benzo-[d]1,3-dioxolene, 2-chloro-1-methoxy-4-phenylbenzene, 2-[(imidazolylmethyl)-amino]-N-[4-(2-phenylethynyl)phenyl]acetamide, 4-phenyl-1-phenoxybenzene, N-(2-amino-ethyl)-[4-(2-phenylethynyl) phenyl]carboxamide, 2-{[(4-fluorophenyl)methyl]-amino}-N-[4-(2-phenylethynyl)phenyl]acetamide, 2-{[(4-methylphenyl)methyl]amino}-N-[4-(2-phenyl-ethynyl) phenyl]acetamide, 4-phenyl-1-(trifluoromethyl)benzene, 1-butyl-4-phenyl-benzene, 2-(cyclohexylamino)-N-[4-(2-phenylethynyl)phenyl]acetamide, 2-(ethyl-methyl-amino)-N-[4-(2-phenylethynyl)phenyl]acetamide, 2-(butylamino)-N-[4-(2-phenyl-ethynyl)-phenyl]acetamide, N-[4-(2-phenylethynyl)phenyl]-2-(4-pyridylamino)-acetamide, N-[4-(2-phenylethynyl)phenyl]-2-(quinuclidin-3-ylamino) acetamide, N-[4-(2-phenyl-ethynyl)phenyl]pyrrolidin-2-yl-carboxamide, 2-amino-3-methyl-N-[4-(2-phenyl-ethynyl)-phenyl]butanamide, 4-(4-phenylbuta-1,3-diynyl) phenylamine, 2-(dimethyl-amino)-N-[4-(4-phenylbuta-1,3-diynyl)phenyl]acetamide, 2-(ethylamino)-N-[4-(4-phenylbuta-1,3-diynyl)-phenyl]acetamide, 4-ethyl-1-phenylbenzene, 1-[4-(2-phenyl-ethynyl)-phenyl]ethan-1-one, N-(1-carbamoyl-2-hydroxypropyl)[4-(4-phenylbuta-1,3-diynyl)-phenyl]-carbox-amide, N-[4-(2-phenylethynyl)

phenyl]propanamide, 4-methoxy-phenyl phenyl ketone, phenyl-N-benzamide, (tert-butoxy)-N-[(4-phenylphenyl)methyl]-carboxamide, 2-(3-phenyl-phenoxy)ethanehydroxamic acid, 3-phenylphenyl propanoate, 1-(4-ethoxyphenyl)-4-methoxybenzene, and [4-(2-phenylethynyl)phenyl]pyrrole.

"Heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenyl-ethynyl)-1,3-dihydropyrimidine-2,4-dione, 4-phenyl-1,2,3-thiadiazole, 2-(2phenyl-ethynyl)pyrazine, 2-phenylthiophene, phenylimidazole, 3-(2-piperazinyl-phenyl)-furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenyl-pyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))-methane, 5-[(4-methylpiperazinyl)methyl]-2-phenylthiophene, 2-(4-ethylphenyl)-thio-phene, 4-methyl-thio-1-(2-thienyl)benzene, 2-(3-nitrophenyl)thiophene, (tert-butoxy)-N-[(5-phenyl-(3-pyridyl))methyl]carboxamide, hydroxy-N-[(5-phenyl(3-pyridyl))methyl]-amide, 2-(phenyl-methylthio)pyridine, and benzylimidazole.

"Heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl-(3-pyrazin-2-yl(4-pyridyl))amine, and dimethyl{2-[2-(5-methylpyrazin-2-yl)ethynyl](4-pyridyl)}amine.

"Optionally substituted" or "substituted" refers to the replacement of hydrogen with a monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, alkyl, haloalkyl, alkyamino, haloalkylamino, alkoxy, haloalkoxy, alkoxy-alkyl, alkylcarbonyl, aminocarbonyl, arylcarbonyl, aralkylcarbonyl, heteroarylcarbonyl, heteroaralkyl-carbonyl, alkylthio, aminoalkyl, cyanoalkyl, aryl and the like.

The substitution group can itself be substituted. The group substituted onto the substitution group can be carboxyl, halo, nitro, amino, cyano, hydroxyl, alkyl, alkoxy, aminocarbonyl, —SR, thioamido, —SO$_3$H, —SO$_2$R, or cycloalkyl, where R is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

Certain of the compounds of the invention comprise asymmetrically substituted carbon atoms. Such asymmetrically substituted carbon atoms can result in the compounds of the invention comprising mixtures of stereoisomers at a particular asymmnetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the tetrahydrocarboline compounds of the invention. These salts can be prepared in situ during the final isolation and purification of the tetrahydrocarboline compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the tetrahydrocarboline compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, and the like.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in Higuchi, T., and V. Stella, "Pro-drugs as Novel Delivery Systems," *A.C.S. Symposium Series* 14, and in "Bioreversible Carriers in Drug Design," in Edward B. Roche (ed.), *American Pharmaceutical Association*, Pergamon Press, 1987, both of which are incorporated herein by reference.

The term "KSP mediated disorder" refers to a disorder that can be beneficially treated by the inhibition of KSP.

The term "cellular proliferative diseases" refers to diseases including, for example, cancer, tumor, hyperplasia, restenosis, cardiac hypertrophy, immune disorder and inflammation.

The term "cancer" refers to cancer diseases that can be beneficially treated by the inhibition of KSP, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to detectably inhibit KSP activity by any of the assays described herein, by other KSP activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, gleevec, herceptin, 5-fluorouracil, leucovorin, carboplatin, cisplatin, taxanes, tezacitabine, cyclophosphamide, vinca alkaloids, imatinib, anthracyclines, rituximab, trastuzumab, topoisomerase I inhibitors, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan, et al, *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formula (I) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-ABL tyrosine kinase. The afflicted patients are responsive to gleevec, a small molecule tyrosine kinase inhibitor, as a result of inhibition of Abl kinase activity. However, many patients with advanced stage disease respond to gleevec initially, but then relapse later due to resistance-conferring mutations in the Abl kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the compounds of formula (I) are used in combination with at least one additional agent, such as gleevec, in the treatment of hematological cancers, such as chronic myelogenous leukemia (CML), to reverse or prevent resistance to the at least one additional agent.

In another aspect of the invention, kits that include one or more compounds of the invention are provided. Representative kits include a tetrahydrocarboline compound of the invention (e.g., a compound of formula (I)) and a package insert or other labeling including directions for treating a cellular proliferative disease by administering an KSP inhibitory amount of the compound.

The present invention will be understood more readily by reference to the following examples, which are provided by way of illustration and are not intended to be limiting of the present invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 µL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine, and triethyl amine. Typical solvents employed for the reverse phase HPLC were varying concentrations of acetonitrile and water with 0.1% trifluoroacetic acid.

The following are abbreviations used in the examples:

| | |
|---|---|
| AcOH: | Acetic acid |
| aq: | Aqueous |
| ATP: | Adenosine triphosphate |
| 9-BBN | 9-Borabicyclo[3.3.1]nonane |
| Boc: | tert-Butoxycarbonyl |
| Celite | Filter agent |
| DAP or Dap: | Diaminopropionate |
| DCM: | Dichloromethane |
| DEAD: | Diethyl azodicarboxylate |
| DIEA: | Diisopropylethylamine |
| DMA | N,N-Dimethylacetamide |
| DMAP | 4-Dimethylaminopyridine |
| DME: | 1,2-Dimethoxyethane |
| DMF: | N,N-Dimethylformamide |
| DMSO: | Dimethyl sulfoxide |
| DPPA: | Diphenyl phosphoryl azide |
| $Et_3N$: | Triethylamine |
| EDC: | N-(3-Dimethylaminopropyl)-N'-ethylcarbodiimide |
| EDCI: | 1-(3-Dimethylaminopropyl)3-ethylcarbodiimide |
| EtOAc: | Ethyl acetate |
| EtOH: | Ethanol |
| Fmoc: | 9-Fluorenylmethoxycarbonyl |
| GC | Gas Chromatography |
| Gly-OH: | Glycine |
| HATU: | O-(7-Azabenzotriaazol-1-yl)-N,N,N'N'-tetramethyluronium hexafluorophosphate |
| HBTU: | 2-(1H-Benzotriazol-1-yl)-1,1,3,3-tetramethyluronium hexafluorophosphate |
| Hex: | Hexane |
| HOAT | 1-Hydroxy-7-azabenzotriazole |
| HOBT: | 1-Hydroxybenzotriazole |
| HPLC: | High performance liquid chromatography |
| NIS | N-Iodosuccinimide |
| $IC_{50}$ value: | The concentration of an inhibitor that causes a 50% reduction in a measured activity. |
| iPrOH: | Isopropanol |
| LC/MS: | Liquid chromatography/mass spectrometry |
| LRMS: | Low resolution mass spectrometry |
| MeOH: | Methanol |
| NaOMe: | Sodium methoxide |
| nm: | Nanometer |
| NMP: | N-Methylpyrrolidone |
| PPA | Polyphosphoric acid |
| $PPh_3$: | Triphenyl phosphine |
| PTFE | Polytetrafluoroethylene |
| PyBOP | Benzotriazole-1-yl-oxy-tris-pyrrolidino-phosphonium |
| RP-HPLC: | Reversed-phase high-performance liquid chromatography |
| RT: | Room temperature |
| sat: | Saturated |
| TEA: | Triethylamine |
| TFA: | Trifluoroacetic acid |
| THF: | Tetrahydrofuran |
| Thr: | Threonine |
| TLC: | Thin layer chromatography |
| Trt-Br: | Triphenylmethyl bromide |

Nomenclature for the Example compounds (Examples 2-11 and Table 1 in Example 12) was provided using ACD Name version 5.07 software (Nov. 14, 2001) or ACD Name Batch version 5.04 (May 28, 2002) available from Advanced Chemistry Development, Inc. Some of the compounds and starting materials were named using standard IUPAC nomenclature.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the above disclosure.

Example 1

The Preparation of a Representative Substituted Tryptomine

In this example, the preparation of a representative substituted tryptomine useful in synthesizing the tetrahydrocarboline compounds of the invention is described. The preparation is illustrated schematically in FIG. 1 and described below with reference to FIG. 1.

Synthesis of phthalimide 1b. To a stirred solution of 4-aminobutyraldehyde diethyl acetal 1a (89.3 mmol) in $CH_3CN$ (100 mL) was added N-carbethoxyphthalimide (93.8 mmol). Once the reaction was complete, the acetonitrile was removed under reduced pressure and the aqueous phase extracted with EtOAc (×3). The organic phase were combined, then washed with water (×4), saturated brine (×3), then dried ($Na_2SO_4$), filtered, and evaporated under reduced pressure to give the title compound 1b, which crystallized on standing.

Synthesis of indole 1d. A mixture of the hydrochloride salt of the hydrazine (1.0 mmol) and 1c (1.0 mmol) and 1b in EtOH (6 mL) and water (1.2 mL) was heated at 85° C. Once the reaction was complete, the EtOH was removed by evaporation under reduced pressure and the aqueous phase treated with sat. aqueous $NaHCO_3$ (5 mL) and then extracted with EtOAc (×3). The organic phase were combined, then washed with $H_2O$ (×3), saturated brine (×3), dried ($Na_2SO_4$), filtered, and evaporated under reduced pressure to give the crude indole 1d.

Synthesis of 1e. To a stirred solution of crude indole 1d (1.0 mmol) in EtOH (4.0 mL) was added anhydrous hydrazine (5.0 mmol). Once the reaction was complete, the mixture was diluted with toluene/EtOH and filtered. The filtrate was evaporated under reduced pressure, and then diluted with EtOH and evaporated under reduced pressure to azeotrope the excess hydrazine. This procedure was repeated 3 times to yield the crude 1e which was used directly as shown in Example 2.

Example 2

Figure 2:
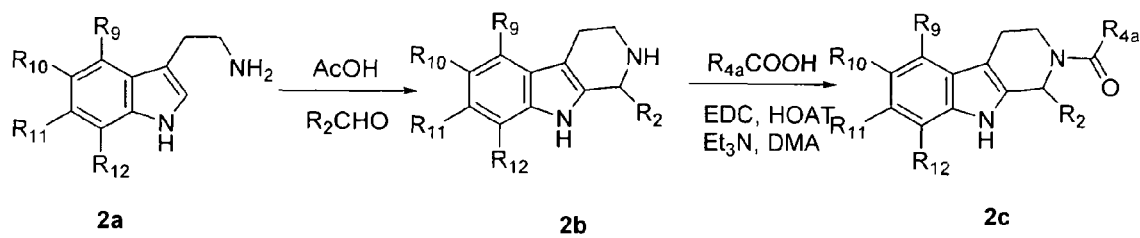
FIG. 2 is a synthetic scheme illustrating the preparation of representative N-acyl substituted tetrahydrocarboline compounds of the invention.

The Preparations of Representative Sulfonamide and N-Acyl Substituted Tetrahydrocarboline Compounds In this example, the preparations of representative sulfonamide and N-acyl tetrahydrocarboline compounds of the invention are described. The preparations are illustrated schematically in FIG. 2 and described below with reference to FIG. 2.

Synthesis of 2b. 2a (1 equiv) was suspended in acetic acid (~0.5 M) and the aldehyde (1.2 equiv) was added. The reaction mixture was stirred at 80° C. for 4 h. The reaction mixture was then cooled down to room temperature. The excess acetic acid was removed by adding ether to the reaction mixture and decanting. The residue was then partitioned between EtOAc and saturated aqueous NaHCO$_3$, the aqueous phase was extracted one additional time with EtOAc, the organic extracts were collected and dried (Na$_2$SO$_4$). Evaporation of the solvent under reduced pressure afforded the desired tetrahydrocarboline 2b, which was used in the next step without further purification.

General procedure for N-sulfonating tetrahydrocarbolines: synthesis of 2d. To a stirred solution of tetrahydro-β-carboline 2b (0.76 mmol) in CH$_2$Cl$_2$ (6 mL) was added DIPEA (2.3 mmol) followed by the appropriate sulfonyl chloride (1.5 mmol). Once the reaction was complete, the mixture was diluted with CH$_2$Cl$_2$ and then washed with saturated aqueous NaHCO$_3$ (×2), H$_2$O (×2), saturated brine (×2), then dried (Na$_2$SO$_4$), filtered, and evaporated under reduced pressure to give the desired 2d.

Example 3

Figure 3:
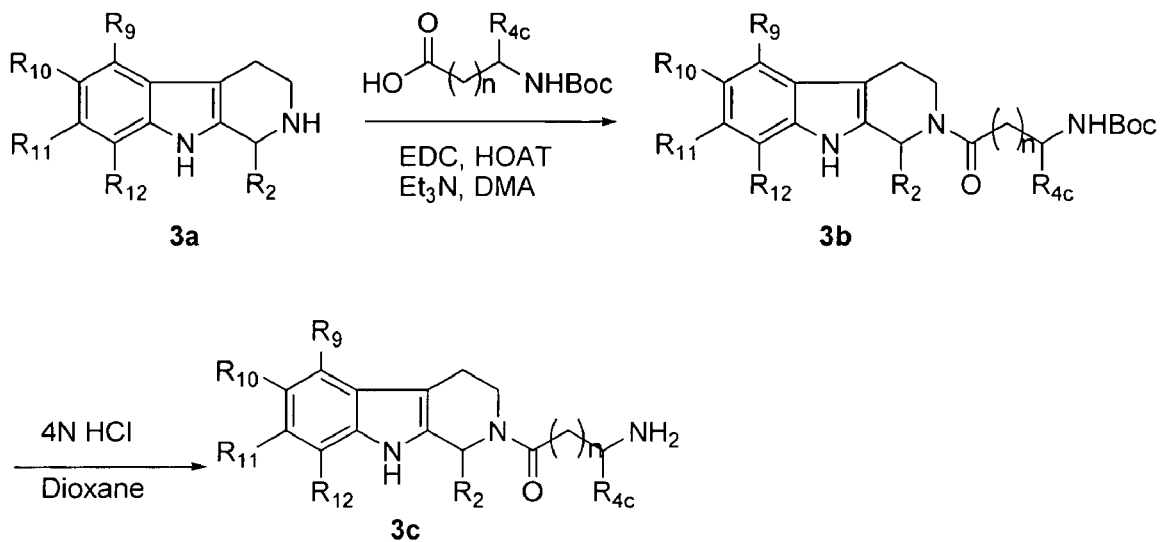
FIG. 3 is a synthetic scheme illustrating the preparation of representative N-aminosubstituted alkylcarbonyl-containing tetrahydrocarboline compounds of the invention.

The Preparation of Representative N-Aminosubstituted Alkylcarbonyl-Containing Tetrahydrocarboline Compounds In this example, the preparation of representative N-aminosubstituted alkylcarbonyl-containing tetrahydrocarboline compounds of the invention is described. The preparation is illustrated schematically in FIG. 3 and described below with reference to FIG. 3.

Synthesis of 3b. 3a (1 equiv) was dissolved in DMA (0.1 M) and N-Boc-CHR$_{4c}$(CH$_2$)n-CO$_2$H (4 equiv) was added. Et$_3$N (4 equiv) was then added, followed by EDC (2 equiv) and HOAT (2 equiv). The reaction mixture was stirred at room temperature overnight, then poured into water. The precipitate 3b was dried and used in the next step without further purification.

Synthesis of 3c. 3b was dissolved in excess 4N HCl in dioxane, and stirred for 20 min. The solvent was evaporated under reduced pressure and the residue was purified by reverse phase preparatory HPLC, to afford 3c.

Example 4

The Preparation of Representative Aryl Substituted Tetrahydrocarboline Compound

Figure 4:
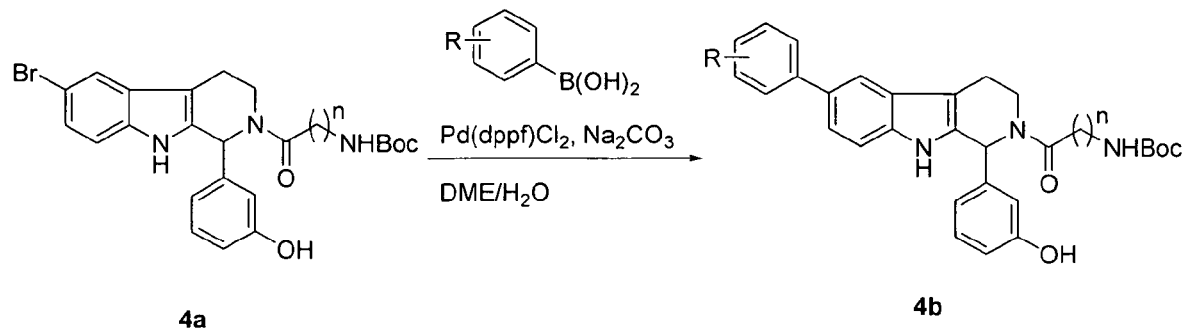
FIG. 4 is a synthetic scheme illustrating the preparation of representative aryl substituted tetrahydrocarboline compounds of the invention.

In this example, the preparation of representative aryl substituted tetrahydrocarboline compounds of the invention is described. The preparation is illustrated schematically in FIG. 4 and described below with reference to FIG. 4.

Synthesis of 4b. To a stirred solution of bromo-tetrahydro-β-carboline 4a (0.1 mmol) in DME (0.5 ml) and H$_2$O (0.17 mL) was added the appropriate boronic acid (0.12 mmol) followed by 2M aqueous Na$_2$CO$_3$ (0.15 mL). The mixture was degassed by bubbling argon through the mixture for 1 minute, and then added Pd(dppf)Cl$_2$ (0.01 mmol). The mixture was heated at 90° C. under argon. Once the reaction was complete, the mixture was allowed to cool and then diluted with EtOAc and H$_2$O. The organics were separated and the aqueous phases extracted with EtOAc (×3). The organic phase were combined then washed with H$_2$O (×2), saturated brine (×2), then dried (Na$_2$SO$_4$), filtered, and evaporated under reduced pressure to give product 4b.

Example 5

Figure 5:
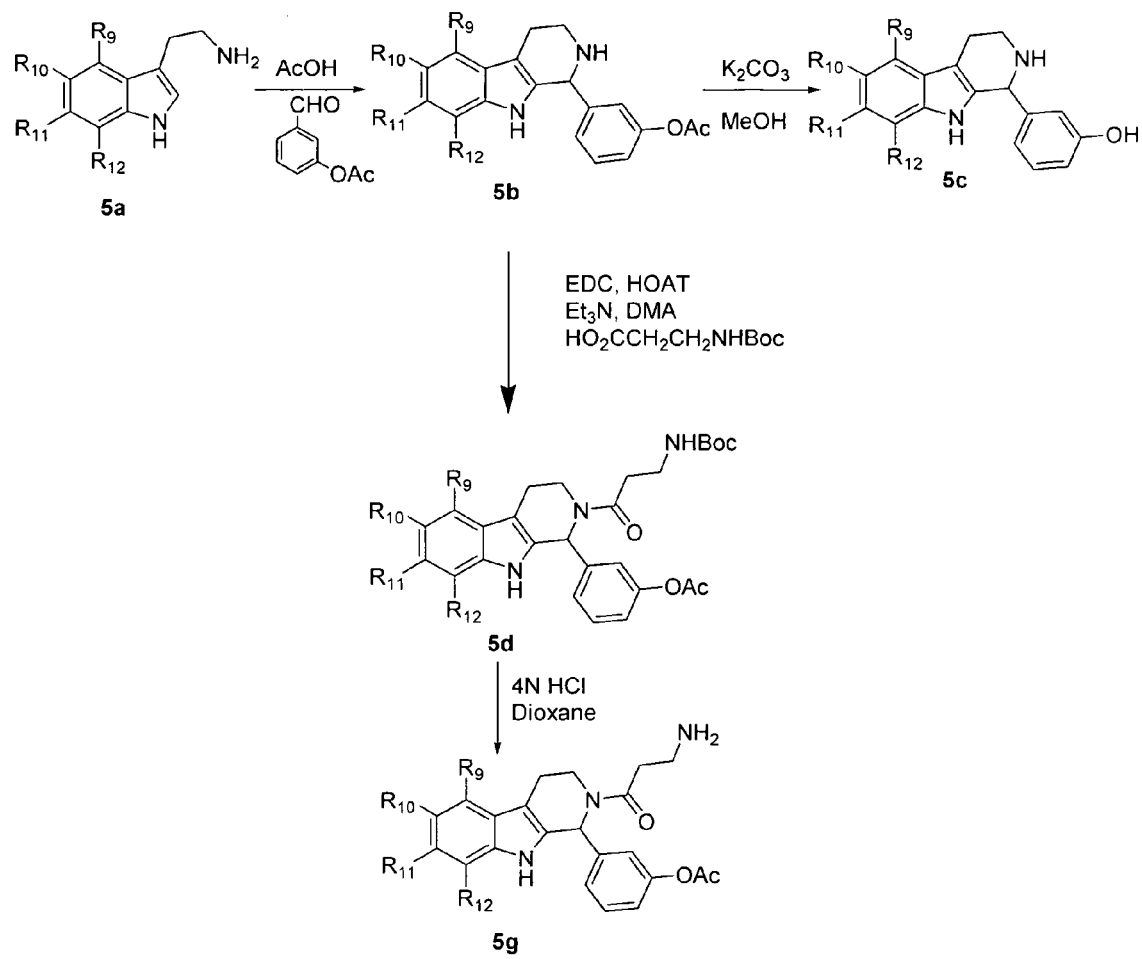
FIG. 5 is a synthetic scheme illustrating the preparation of representative 3-hydroxyphenyl substituted tetrahydrocarboline compounds of the invention.

The Preparation of Representative 3-Hydroxyphenyl Substituted Tetrahydrocarboline Compounds In this example, the preparations of representative 3-hydroxyphenyl substituted tetrahydrocarboline compounds of the invention are described. The preparations are illustrated schematically in FIG. 5 and described below with reference to FIG. 5.

5a was synthesized as described in Example 1. 5b was synthesized using similar procedure described in Example 2 for 2b.

Synthesis of 5c. 5b (1 equiv) was dissolved in MeOH, and solid K$_2$CO$_3$ (3 equiv) was added. The reaction mixture was stirred at room temperature for 1 h, then filtered and evaporated. Purification by reverse phase preparatory HPLC afforded 5c.

Synthesis of 5d and 5g. 5b (1 equiv) was dissolved in DMA (0.1 M) and BocNH(CH$_2$)$_2$CO$_2$H (3 equiv) was added. Et$_3$N (4 equiv) was then added, followed by EDC (2 equiv) and HOAT (2 equiv). The reaction mixture was stirred at room temperature overnight, then poured into water. A precipitate formed, which was filtered and dried to yield 5d. Removal of the Boc group using the procedure described above for 3c, and purification by reverse phase preparatory HPLC afforded 5g.

Example 6

Figure 6:
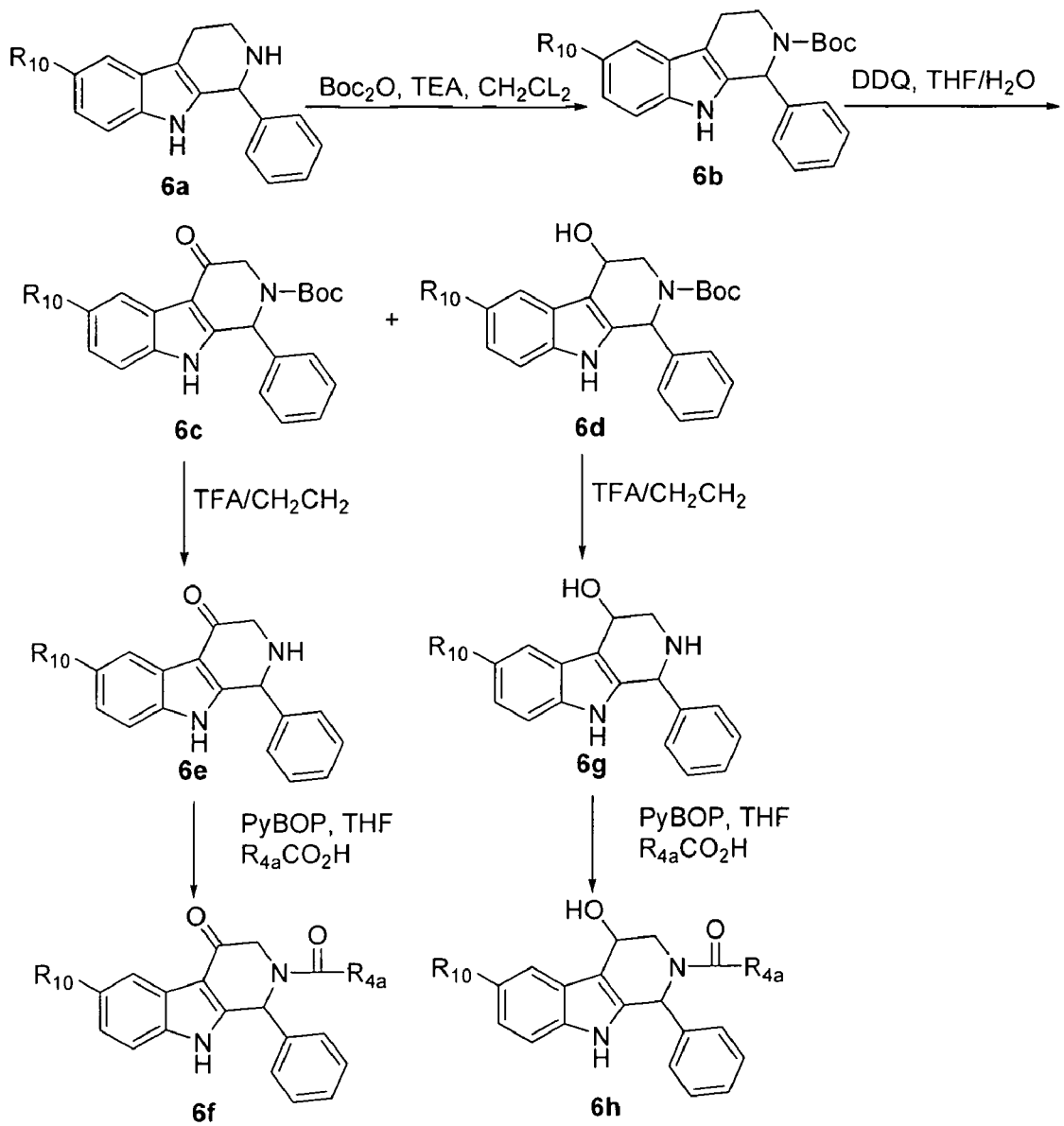
FIG. 6 is a synthetic scheme illustrating the preparation of representative tetrahydrocarboline-4-one and tetrahydrocarboline-4-ol compounds of the invention.

The Preparation of Representative Tetrahydrocarboline-4-one and Tetrahydrocarboline-4-ol Compounds In this example, the preparations of representative tetrahydrocarboline-4-one and tetrahydrocarboline-4-ol compounds of the invention are described. The preparations are illustrated schematically in FIG. 6 and described below with reference to FIG. 6.

6a was synthesized using similar procedure as described in Example 2.

Synthesis of 6b. To a mixture of 6a (1 equiv) and triethyl amine (2 equiv) in dichloromethane was added a solution of Boc$_2$O (2 equiv) in dichloromethane at 0° C. The mixture was allowed to stir at room temperature overnight and diluted with dichloromethane. The organic phase was washed with water, dried over Na$_2$SO$_4$. The solvent was removed and purified to give 6b.

Synthesis of 6c and 6d. Substituted 1,2,3,4-tetrahydro-beta-carboline-2-carboxylic acid tert-butyl ester 6b (1 equiv) and DDQ (2.5 equiv) were mixed together until a uniform color was observed. The mixture of powders was cooled to −78° C. The solvent mixture (THF/H$_2$O, 9:1) was added slowly to the mixture of powders. The slurry was stirred and allowed to warm to room temperature. The solution was then poured into aqueous NaOH (1N) and extracted with EtOAc. The combined organic layers were washed with H$_2$O, dried and this dried mixture of 6c and 6d were separated by flash chromatography.

Synthesis of 6e. To a solution of 6c in DCM was added 10% TFA at 0° C. The mixture was stirred at room temperature for 4 h and then concentrated to give 6e as a TFA salt.

Synthesis of 6f. To a solution of 6e (1 equiv) in THF was added PyBOP (1.2 equiv), carboxylic acid (1.2 equiv) and Et$_3$N (2.2 equiv). After being stirred overnight, the solvent was removed to give a residue, which was purified to give 6f.

Synthesis of 6g. To a solution of 6d in DCM was added 10% TFA at 0° C. The mixture was stirred at room temperature for 4 h and then concentrated to give 6g as TFA salt.

Synthesis of 6h. To a solution of 6g (1 equiv) in THF was added PyBOP (1.2 equiv), acid (1.2 equiv) and Et₃N (2.2 equiv). After being stirred overnight, solvent was removed to give a residue, which was purified to give 6h.

Example 7

The Preparation of Representative Tetrahydrocarboline Compounds

In this example, the preparations of a variety of representative tetrahydrocarboline compounds listed in Table 1 are described.

General procedure for the preparation of 1,2,3,4-tetrahydro-beta-carboline. A mixture of substituted tryptamine (1 equiv) and 3-hydroxybenzaldehyde (1.05 equiv) in acetic acid was heated at 90° C. overnight. After cooling to room temperature, the solid was filtered and washed twice with acetic acid, and dried to give substituted 1-(3-hydroxyphenyl)-1,2,3,4-tetrahydro-beta-carboline.

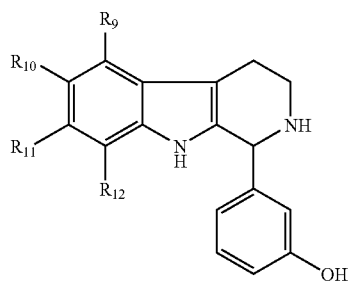

The following compounds were prepared according to the above procedure.

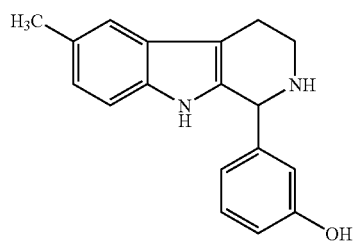

3-(6-methyl-1,2,3,4-tetrahydrobeta-carbolinyl)phenol

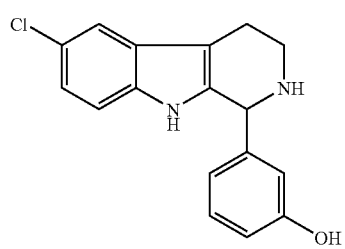

3-(6-chloro-1,2,3,4-tetrahydrobeta-carbolinyl)phenol

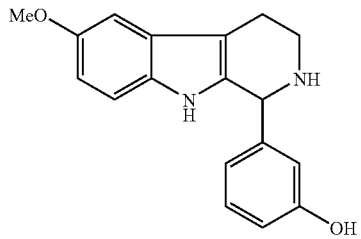

3-(6-methoxy-1,2,3,4-tetrahydrobeta-carbolinyl)phenol

General procedure for the preparation of 2-acyl-1-(3-hydroxyphenyl)-6-substituted-1,2,3,4-tetrahydro-beta-carboline. To a solution of 6-substituted-1-(3-hydroxyphenyl)-1,2,3,4-tetrahydro-beta-carboline (1 equiv) in THF was added Et₃N (2.2 equiv) and acyl chloride (1.1 equiv). After one hour, the product was purified on silica gel to give 2-acyl-1-(3-hydroxyphenyl)-6-substituted-1,2,3,4-tetrahydro-beta-carboline as shown below.

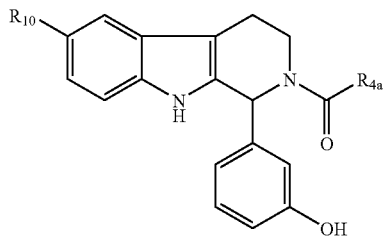

3-(2-acetyl-6-methyl-2,3,4,9-tetrahydro-1H-beta-carbolin-1-yl)phenol 1. To a solution of 6-methyl-1-(3-hydroxyphenyl)-1,2,3,4-tetrahydro-beta-carboline (1 equiv) in THF was added Et₃N (2.2 equiv) and acetic anhydride (1.2 equiv). After one hour, the solution was purified by prep-HPLC to give 3-(2-acetyl-6-methyl-2,3,4,9-tetrahydro-1H-beta-carbolin-1-yl)phenol 1.

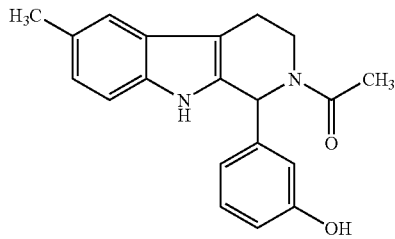

The following compounds were prepared according to the above procedure.

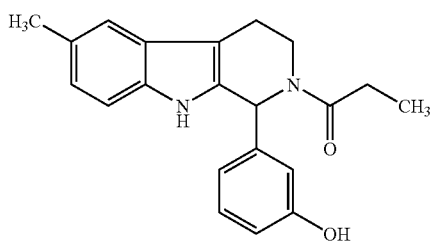

3-(6-methyl-2-propionyl-2,3,4,9-tetrahydro-1H-beta-carbolin-1-yl)phenol 2

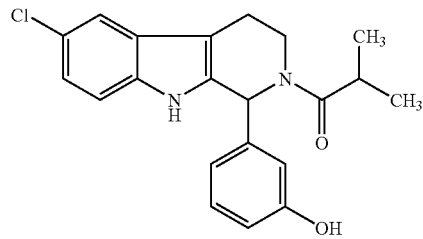

3-(2-acetyl-6-chloro-2,3,4,9-tetrahydro-1H-beta-carbolin-1-yl)phenol 5

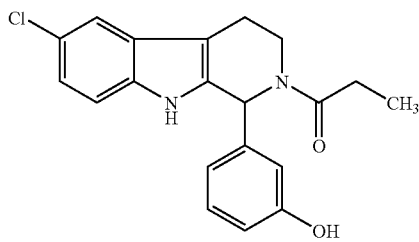

3-(2-acetyl-6-methoxy-2,3,4,9-tetrahydro-1H-beta-carbolin-1-yl)phenol 3

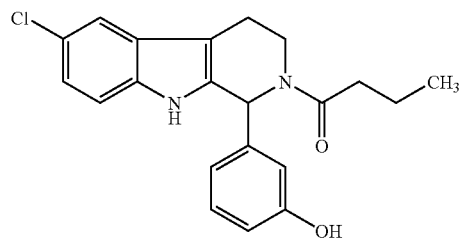

3-(6-chloro-2-isobutyryl-2,3,4,9-tetrahydro-1H-beta-carbolin-1-yl)phenol 6

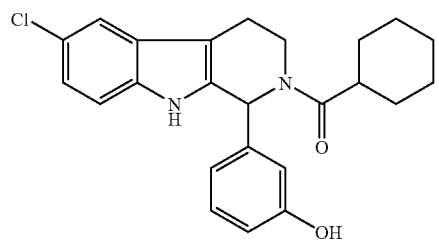

3-(2-butyryl-6-chloro-2,3,4,9-tetrahydro-1H-beta-carbolin-1-yl)phenol 7

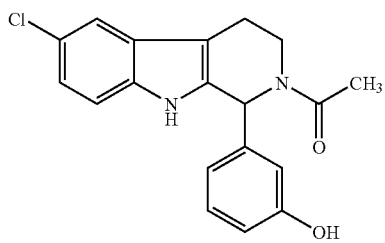

3-(6-chloro-2-propionyl-2,3,4,9-tetrahydro-1H-beta-carbolin-1-yl)phenol 4

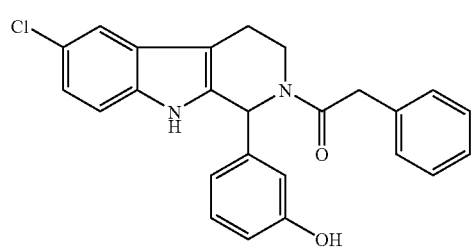

3-[6-chloro-2-(cyclohexylcarbonyl)-2,3,4,9-tetrahydro-1H-beta-carbolin-1-yl]phenol 8

3-[6-chloro-2-(phenylacetyl)-2,3,4,9-tetrahydro-1H-beta-carbolin-1-yl]phenol 9

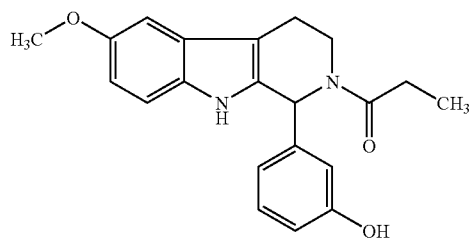

3-(6-methoxy-2-propionyl-2,3,4,9-tetrahydro-1H-beta-carbolin-1-yl)phenol 10

3-[6-methyl-2-(morpholin-4-ylacetyl)-2,3,4,9-tetrahydro-1H-beta-carbolin-1-yl]phenol 16. To a solution of 6-methyl-1-(3-hydroxyphenyl)-1,2,3,4-tetrahydro-beta-carboline (1 equiv) in THF was added Et$_3$N (2.2 equiv) and alpha-bromoacetyl bromide (1.2 equiv). The solution was stirred at room temperature for 30 min to give crude 2-bromo-1-[1-(3-hydroxyphenyl)-6-methyl-(1,2,3,4-tetrahydro-beta-carbolin-2-yl)]ethan-1-one. To the solution was added morpholine (2 equiv). The solution was stirred overnight and purified to give 3-[6-methyl-2-(morpholin-4-ylacetyl)-2,3,4,9-tetrahydro-1H-beta-carbolin-1-yl]phenol 16.

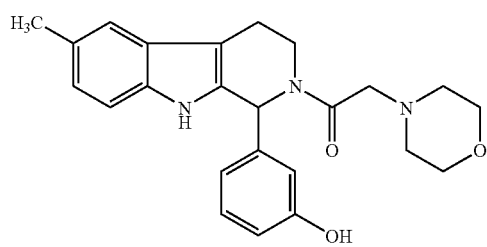

The following compounds were prepared according to the above procedure.

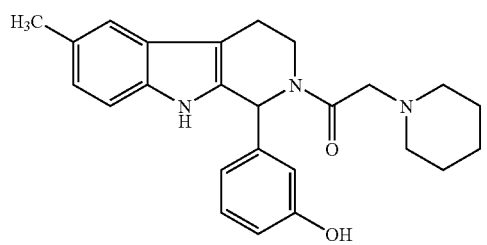

3-[6-methyl-2-(piperidin-1-ylacetyl)-2,3,4,9-tetrahydro-1H-beta-carbolin-1-yl]phenol 17

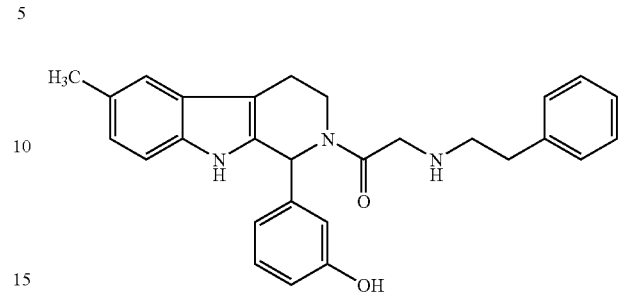

3-{6-methyl-2-[N-(2-phenylethyl)glycyl]-2,3,4,9-tetrahydro-1H-beta-carbolin-1-yl}phenol 18

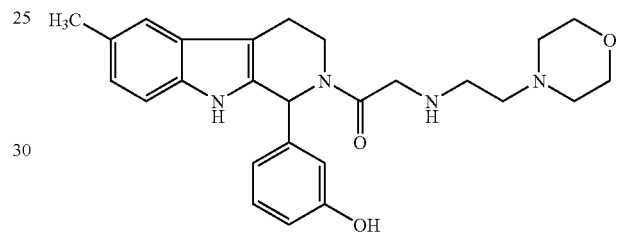

3-{6-methyl-2-[N-(2-morpholin-4-ylethyl)glycyl]-2,3,4,9-tetrahydro-1H-beta-carbolin-1-yl}phenol 19

3-{2-[N-(tert-butoxycarbonyl)-glycyl]-6-methyl-2,3,4,9-tetrahydro-1H-beta-carbolin-1-yl}phenol 11. To a solution of 6-methyl-1-(3-hydroxyphenyl)-1,2,3,4-tetrahydro-beta-carboline (1 equiv) in THF was added Et$_3$N (2.2 equiv) and Boc-Gly-OSu (1.2 equiv). After 2 h, the solvent was removed to give a residue, which was purified via prep-HPLC to give 3-{2-[N-(tert-butoxycarbonyl)-glycyl]-6-methyl-2,3,4,9-tetrahydro-1H-beta-carbolin-1-yl)}phenol 11.

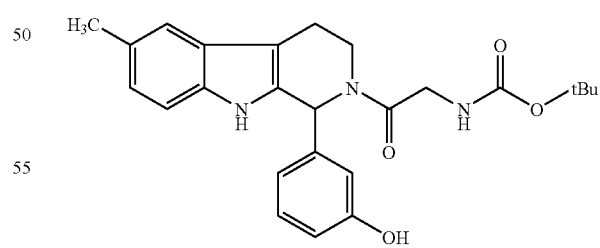

3-(2-glycyl-6-methyl-2,3,4,9-tetrahydro-1H-beta-carbolin-1-yl)phenol 14. (tert-Butoxy)-N-{2-[1-(3-hydroxyphenyl)-6-methyl-(1,2,3,4-tetrahydro-beta-carbolin-2-yl)]-2-oxoethyl}carboxamide 11 was treated with HCl in dioxane (4 N, 10 equiv) for 30 min, and the solvent was removed to give 3-(2-glycyl-6-methyl-2,3,4,9-tetrahydro-1H-beta-carbolin-1-yl)phenol 14 as its HCl salt.

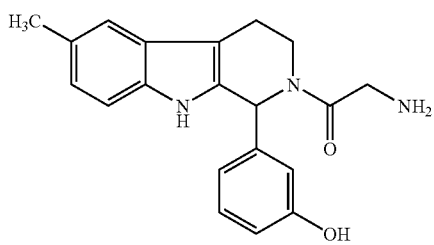

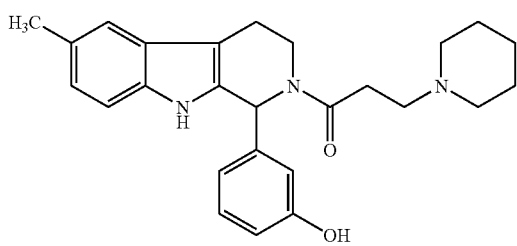

General procedure for coupling of beta-carboline with carboxylic acid: 3-{2-[N-(tert-butoxycarbonyl)-beta-alanyl]-6-methyl-2,3,4,9-tetrahydro-1H-beta-carbolin-1-yl}phenol 12. To a solution of 6-methyl-1-(3-hydroxyphenyl)-1,2,3,4-tetrahydrobeta-carboline (1 equiv) in THF was added PyBOP (1.2 equiv), Boc-beta-Ala-OH (1.2 equiv), and Et₃N (2.2 equiv). After being stirred overnight, solvent was removed to give a residue, which was purified to give 3-{2-[N-(tert-butoxycarbonyl)-beta-alanyl]-6-methyl-2,3,4,9-tetrahydro-1H-beta-carbolin-1-yl}phenol 12.

(tert-butoxy)-N-{3-[1-(3-hydroxyphenyl)-6-methyl-(1,2,3,4-tetrahydro-beta-carbolin-2-yl)]-3-oxopropyl}carboxamide The following compound was prepared according to the above procedure.

3-[2-(N,N-diethyl-beta-alanyl)-6-methyl-2,3,4,9-tetrahydro-1H-beta-carbolin-1-yl]phenol 20

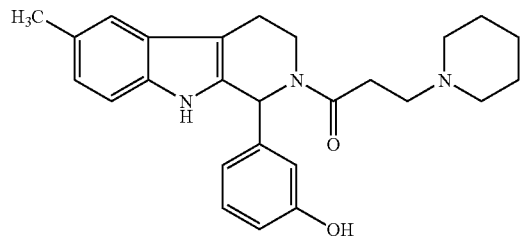

3-[6-methyl-2-(3-piperidin-1-ylpropanoyl)-2,3,4,9-tetrahydro-1H-beta-carbolin-1-yl]phenol 21

(tert-butoxy)-N-{4-[1-(3-hydroxyphenyl)-6-methyl-(1,2,3,4-tetrahydrobeta-carbolin-2-yl)]-4-oxobutyl}carboxamide 3-(2-N-tert-butoxycarbonyl-beta-alanyl-6-chloro-2,3,4,9-tetrahydro-1H-beta-carbolin-1-yl)phenol 3-(2-beta-alanyl-6-methyl-2,3,4,9-tetrahydro-1H-beta-carbolin-1-yl)phenol 15. (tert-Butoxy)-N-{3-[1-(3-hydroxyphenyl)-6-methyl-(1,2,3,4-tetrahydro-beta-carbolin-2-yl)]-3-oxopropyl}carboxamide was treated with HCl in dioxane (4 N, 10 equiv) for 30 min, and the solvent was removed to give 3-(2-beta-alanyl-6-methyl-2,3,4,9-tetrahydro-1H-beta-carbolin-1-yl)phenol 15 as its HCl salt.

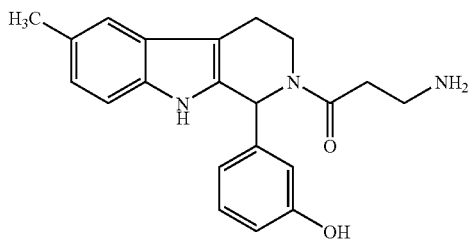

3-(2-beta-alanyl-6-chloro-2,3,49-tetrahydro-1H-beta-carbolin-1-yl)phenol 23. (tert-Butoxy)-N-{3-[1-(3-hydroxyphenyl)-6-chloro-(1,2,3,4-tetrahydro-beta-carbolin-2-yl)]-3-oxopropyl}carboxamide was treated with HCl in dioxane (4 N, 10 equiv) for 30 min, and the solvent was removed to give a residue which was purified to yield 3-(2-beta-alanyl-6-chloro-2,3,4,9-tetrahydro-1H-beta-carbolin-1-yl)phenol 23.

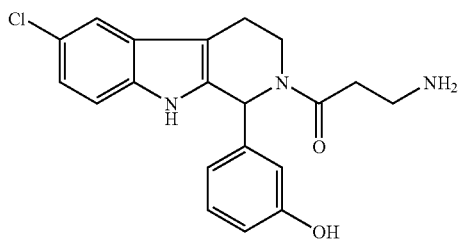

Example 8

The Preparation of a Representative Tetrahydrocarboline Compound

Compound 98

Figure 7:
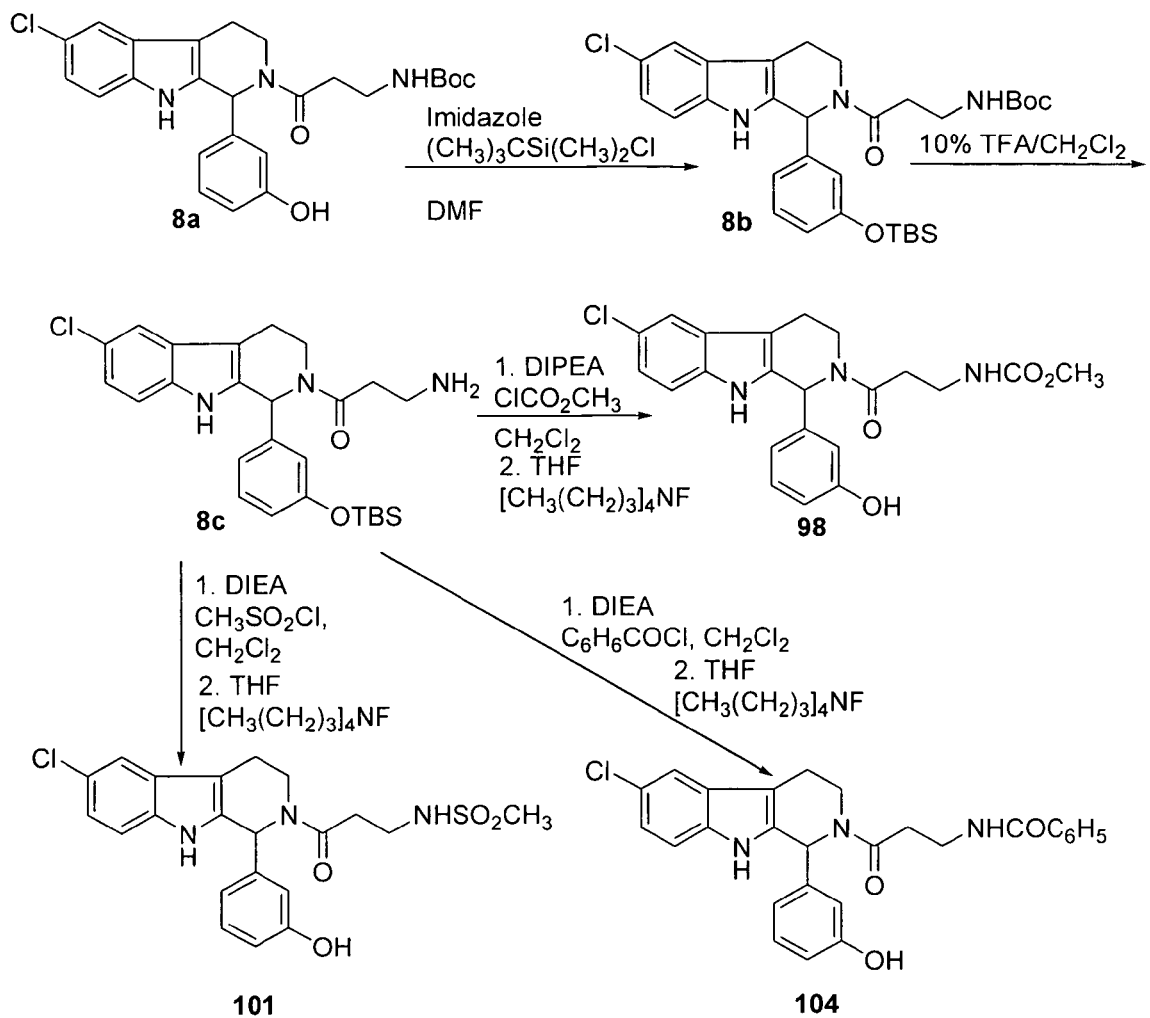
FIG. 7 is a synthetic scheme illustrating the preparation of representative carboxy and amide substituted tetrahydrocarboline compounds of the invention.

In this example, the preparation of a representative tetrahydrocarboline compound, Compound 98 in Table 1, is described. The preparation is illustrated schematically in FIG. 7 and described below with reference to FIG. 7.

Synthesis of TBS protected Phenol 8b. To a stirred solution of phenol 8a (1.2 mmol) in DMF (2.0 mL) was added imidazole (3.67 mmol) followed by tert-butyldimethylsilyl chloride (1.52 mmol). Once the reaction was complete, the mixture was partitioned between EtOAc and saturated NH$_4$Cl. The organic phase was separated, then washed with saturated NH$_4$Cl (×3), water (×2), saturated brine (×3), then dried (Na$_2$SO$_4$), filtered, and evaporated under reduced pressure to give compound 8b, which was used directly in the next step.

Synthesis of amine 8c. Boc-amine 8b was treated with 10% TFA/CH$_2$Cl$_2$. Once the reaction was complete, the solvent was removed by evaporation under reduced pressure and the residue partitioned between EtOAc and sat. aqueous NaHCO$_3$. The organic phase was separated, then washed with sat. aqueous NaHCO$_3$ (×3), H$_2$O (×3), saturated brine (×3), then dried (Na$_2$SO$_4$), filtered, and evaporated under reduced pressure to give the free amine 8c.

Synthesis of 98. To a stirred solution of TBS protected tetrahydro-β-carboline 8c (0.0165 mmol) in CH$_2$Cl$_2$ (0.3 mL) was added DIPEA (0.033 mmol) followed by methyl chloroformate (0.02 mmol). Once the reaction was complete, the mixture was concentrated in vacuo. The residue was then dissolved in THF (0.3 mL) and treated with 1M tetra-butyl ammonium fluoride (0.033 mmol). Once the reaction was complete, the mixture was diluted with EtOAc and then washed with saturated aqueous NaHCO$_3$ (×2), H$_2$O (×2), saturated brine (×2), then dried (Na$_2$SO$_4$), filtered, and evaporated under reduced pressure. The residue was purified by reverse phase prep HPLC to give Compound 98.

Compounds 99 and 100 were synthesized using procedures similar to the procedure for the synthesis of Compound 98.

Example 9

The Preparation of a Representative Tetrahydrocarboline Compound

Compound 101

In this example, the preparation of a representative tetrahydrocarboline compound, Compound 101 in Table 1, is described. The preparation is illustrated schematically in FIG. 7 and described below with reference to FIG. 7.

To a stirred solution of TBS protected tetrahydro-β-carboline 8c from Example 8 (0.0165 mmol) in CH$_2$Cl$_2$ (0.3 mL) was added DIPEA (0.033 mmol) followed by the appropriate sulfonyl chloride (e.g., methyl sulfonyl chloride) (0.02 mmol). Once the reaction was complete, the mixture was concentrated in vacuo. The residue was then dissolved in THF (0.3 mL) and treated with 1M tetra-butyl ammonium fluoride (0.033 mmol). Once the reaction was complete, the mixture was diluted with EtOAc and then washed with saturated aqueous NaHCO$_3$ (×2), H$_2$O (×2), saturated brine (×2), then dried (Na$_2$SO$_4$), filtered, and evaporated under reduced pressure. The residue was purified by reverse phase prep HPLC to give Compound 101.

Compounds 102 and 103 were synthesized using procedures similar to the procedure for the synthesis of Compound 101.

Example 10

The Preparation of a Representative Tetrahydrocarboline Compound

Compound 104

In this example, the preparation of a representative tetrahydrocarboline compound, Compound 104 in Table 1, is described. The preparation is illustrated schematically in FIG. 7 and described below with reference to FIG. 7.

To a stirred solution of TBS protected tetrahydro-β-carboline 8c from Example 8 (0.0165 mmol) in CH$_2$Cl$_2$ (0.3 mL) was added DIPEA (0.033 mmol) followed by the appropriate acid chloride (e.g., benzoyl chloride) (0.02 mmol). Once the reaction was complete, the mixture was concentrated in vacuo. The residue was then dissolved in THF (0.3 mL) and treated with 1M tetra-butyl ammonium fluoride (0.033 mmol). Once the reaction was complete, the mixture was diluted with EtOAc and then washed with saturated aqueous NaHCO$_3$ (×2), H$_2$O (×2), saturated brine (×2), then dried (Na$_2$SO$_4$), filtered, and evaporated under reduced pressure. The residue was purified by reverse phase prep HPLC to give Compound 104.

Compounds 105 and 106 were synthesized using procedures similar to the procedure for the synthesis of Compound 104.

Example 11

Figure 8:
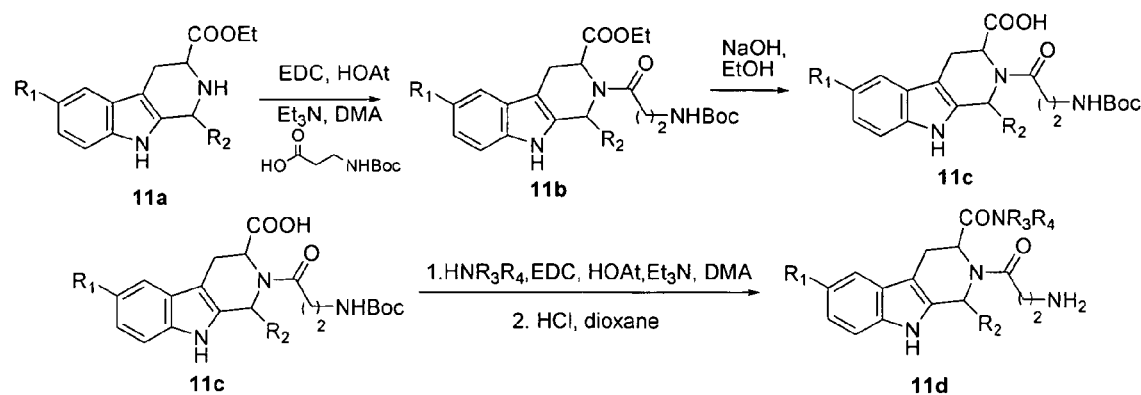
FIG. 8 is a synthetic scheme illustrating the preparation of representative carbamate, sulfonamide, and amide substituted tetrahydrocarboline compounds of the invention.

General Procedure for 2-(3-Aminopropanoyl)-2,3,4,9-tetrahydro-1H-beta-carboline-3-carboxamides In this example, the preparation of representative tetrahydrocarboline compounds, Compounds 110-112, 138, and 139 in Table 1, is described. The preparation is illustrated schematically in FIG. 8 and described below with reference to FIG. 8.

The ethyl ester of 11a (1 equiv) was dissolved in DMA (0.1 M) and BocNH(CH$_2$)$_2$CO$_2$H (3 equiv) was added. Et$_3$N (4 equiv) was then added, followed by EDC (2 equiv) and HOAT (2 equiv). The reaction mixture was stirred at room temperature overnight, then poured into water. A precipitate formed, which was filtered and dried to yield 11b.

Ethyl ester 11b was then hydrolyzed using NaOH in EtOH and the resulting carboxylic acid 11c was coupled with various amines following a procedure identical to the one described for the synthesis of 11b. Removal of the Boc using the same deprotection condition as in the synthesis of 3c, and purification by reverse phase preparatory HPLC afforded the final compounds 11d. Compounds 110-112, 138, and 139 were synthesized in this manner.

Example 12

Representative Tetrahydrocarboline Compounds

Representative tetrahydrocarboline compound compounds of the invention are shown in Table 1. In Table 1, MH+ refers to the molecular ion observed by mass spectrometry.

TABLE 1

Representative Tetrahydrocarboline Compounds.

| Compound | Structure | Name | MH+ |
|---|---|---|---|
| 1 | 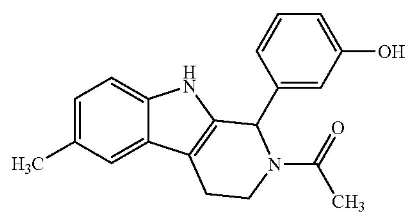 | 3-(2-acetyl-6-methyl-2,3,4,9-tetrahydro-1H-beta-carbolin-1-yl)phenol | 321.4 |
| 2 | 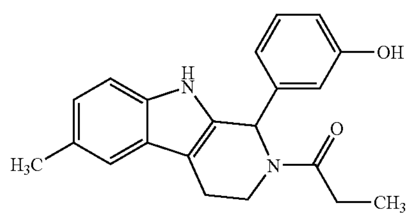 | 3-(6-methyl-2-propionyl-2,3,4,9-tetrahydro-1H-beta-carbolin-1-yl)phenol | 335.4 |
| 3 | 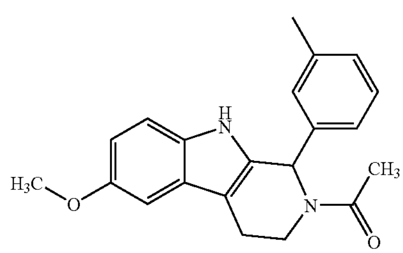 | 3-(2-acetyl-6-methoxy-2,3,4,9-tetrahydro-1H-beta-carbolin-1-yl)phenol | 337.3 |
| 4 | 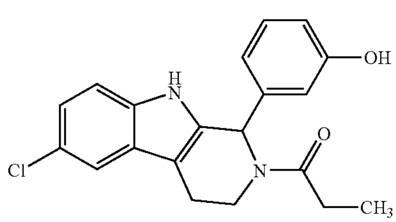 | 3-(6-chloro-2-propionyl-2,3,4,9-tetrahydro-1H-beta-carbolin-1-yl)phenol | 355.8 |

TABLE 1-continued

Representative Tetrahydrocarboline Compounds.

| Compound | Structure | Name | MH+ |
|---|---|---|---|
| 5 | 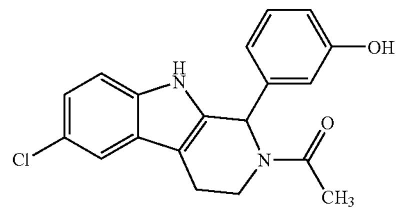 | 3-(2-acetyl-6-chloro-2,3,4,9-tetrahydro-1H-beta-carbolin-1-yl)phenol | 341.8 |
| 6 | 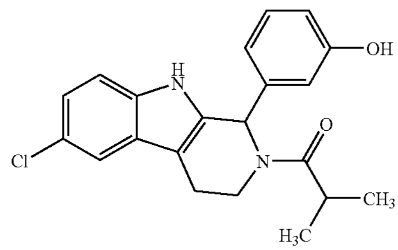 | 3-(6-chloro-2-isobutyryl-2,3,4,9-tetrahydro-1H-beta-carbolin-1-yl)phenol | 369.8 |
| 7 | 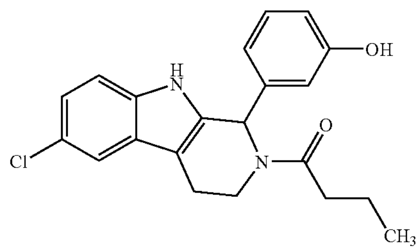 | 3-(2-butyryl-6-chloro-2,3,4,9-tetrahydro-1H-beta-carbolin-1-yl)phenol | 369.8 |
| 8 | 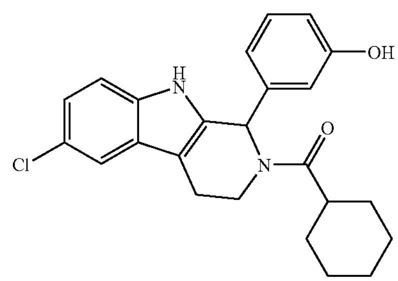 | 3-[6-chloro-2-(cyclohexylcarbonyl)-2,3,4,9-tetrahydro-1H-beta-carbolin-1-yl]phenol | 409.9 |
| 9 | 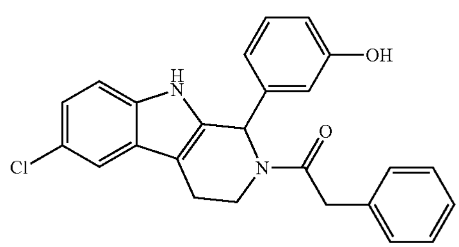 | 3-[6-chloro-2-(phenylacetyl)-2,3,4,9-tetrahydro-1H-beta-carbolin-1-yl]phenol | 417.9 |
| 10 | 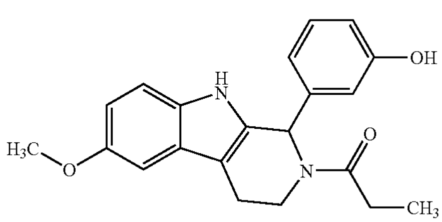 | 3-(6-methoxy-2-propionyl-2,3,4,9-tetrahydro-1H-beta-carbolin-1-yl)phenol | 351.4 |

TABLE 1-continued

Representative Tetrahydrocarboline Compounds.

| Compound | Structure | Name | MH+ |
|---|---|---|---|
| 11 | 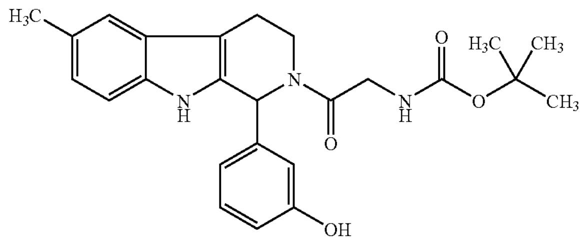 | 3-{2-[N-(tert-butoxycarbonyl)-glycyl]-6-methyl-2,3,4,9-tetrahydro-1H-beta-carbolin-1-yl}phenol | 436.5 |
| 12 | 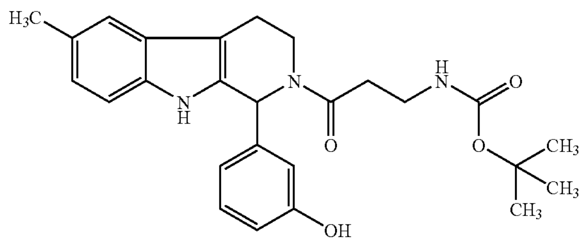 | 3-{2-[N-(tert-butoxycarbonyl)-beta-alanyl]-6-methyl-2,3,4,9-tetrahydro-1H-beta-carbolin-1-yl}phenol | 450.5 |
| 13 | 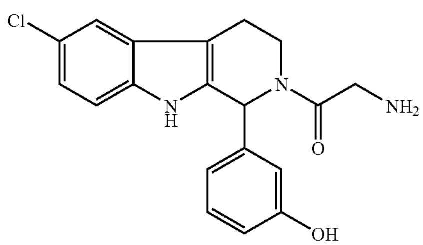 | 3-(6-chloro-2-glycyl-2,3,4,9-tetrahydro-1H-beta-carbolin-1-yl)phenol | 356.8 |
| 14 | 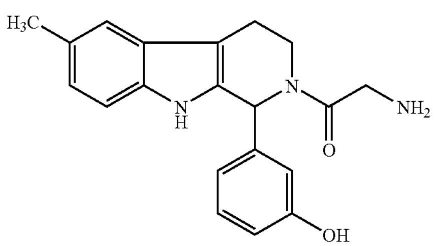 | 3-(2-glycyl-6-methyl-2,3,4,9-tetrahydro-1H-beta-carbolin-1-yl)phenol | 336.4 |
| 15 | 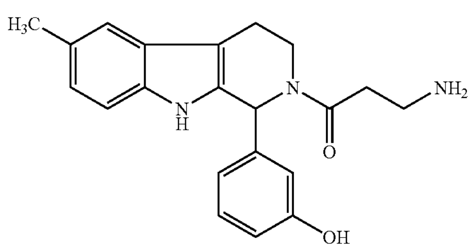 | 3-(2-beta-alanyl-6-methyl-2,3,4,9-tetrahydro-1H-beta-carbolin-1-yl)phenol | 350.4 |
| 16 | 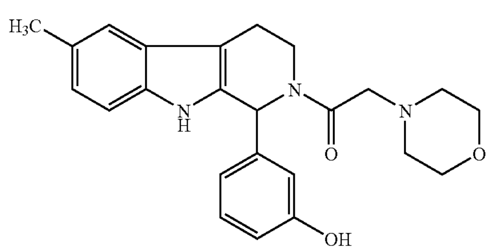 | 3-[6-methyl-2-(morpholin-4-ylacetyl)-2,3,4,9-tetrahydro-1H-beta-carbolin-1-yl]phenol | 406.4 |

TABLE 1-continued

Representative Tetrahydrocarboline Compounds.

| Compound | Structure | Name | MH+ |
|---|---|---|---|
| 17 | 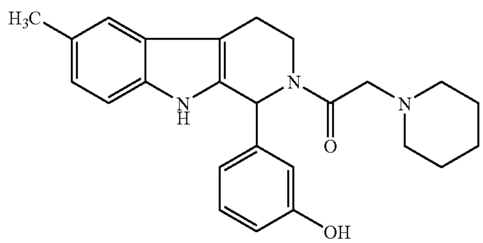 | 3-[6-methyl-2-(piperidin-1-ylacetyl)-2,3,4,9-tetrahydro-1H-beta-carbolin-1-yl]phenol | 404.5 |
| 18 | 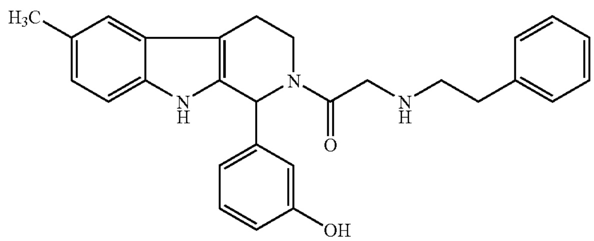 | 3-{6-methyl-2-[N-(2-phenylethyl)glycyl]-2,3,4,9-tetrahydro-1H-beta-carbolin-1-yl}phenol | 440.5 |
| 19 | 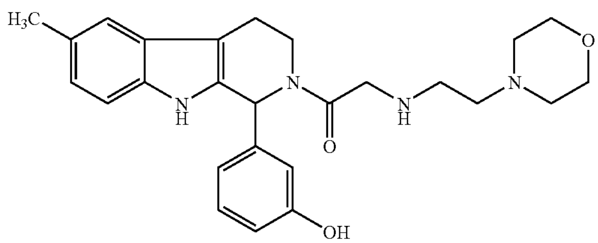 | 3-{6-methyl-2-[N-(2-morpholin-4-ylethyl)glycyl]-2,3,4,9-tetrahydro-1H-beta-carbolin-1-yl}phenol | 449.5 |
| 20 | 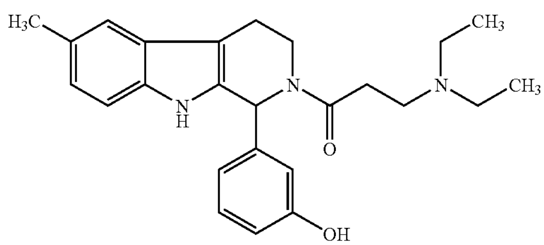 | 3-[2-(N,N-diethyl-beta-alanyl)-6-methyl-2,3,4,9-tetrahydro-1H-beta-carbolin-1-yl]phenol | 406.5 |
| 21 | 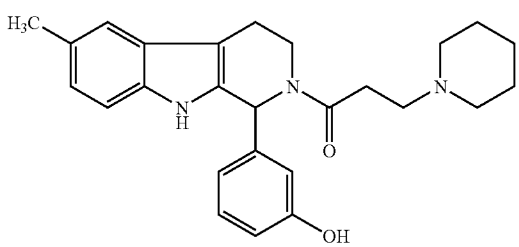 | 3-[6-methyl-2-(3-piperidin-1-ylpropanoyl)-2,3,4,9-tetrahydro-1H-beta-carbolin-1-yl]phenol | 418.5 |
| 22 | 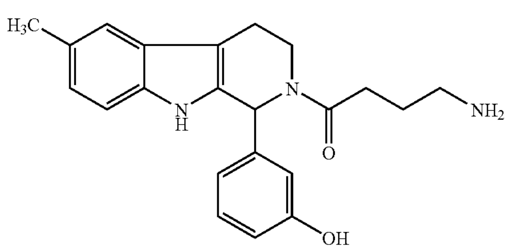 | 3-[2-(4-aminobutanoyl)-6-methyl-2,3,4,9-tetrahydro-1H-beta-carbolin-1-yl]phenol | 364.4 |

TABLE 1-continued

Representative Tetrahydrocarboline Compounds.

| Compound | Structure | Name | MH+ |
|---|---|---|---|
| 23 | 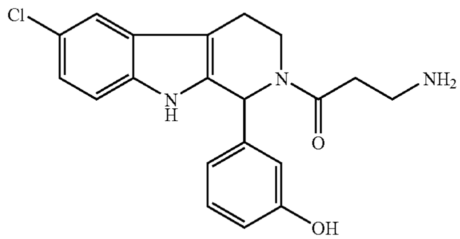 | 3-(2-beta-alanyl-6-chloro-2,3,4,9-tetrahydro-1H-beta-carbolin-1-yl)phenol | 370.8 |
| 24 | 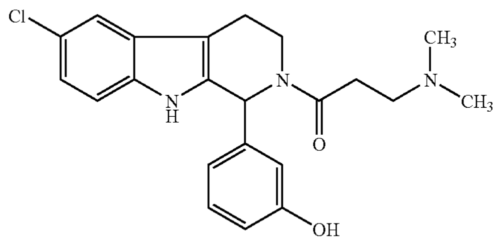 | 3-[6-chloro-2-(N,N-dimethyl-beta-alanyl)-2,3,4,9-tetrahydro-1H-beta-carbolin-1-yl]phenol | 398.9 |
| 25 | 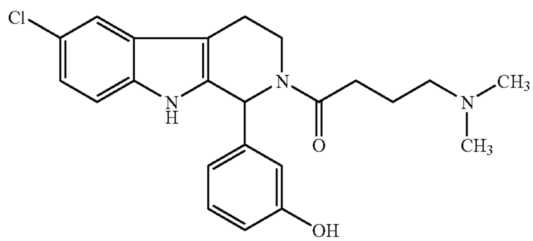 | 3-{6-chloro-2-[4-(dimethylamino)butanoyl]-2,3,4,9-tetrahydro-1H-beta-carbolin-1-yl}phenol | 412.9 |
| 26 | 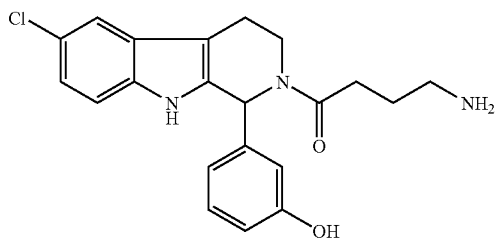 | 3-[2-(4-aminobutanoyl)-6-chloro-2,3,4,9-tetrahydro-1H-beta-carbolin-1-yl]phenol | 384.8 |
| 27 | 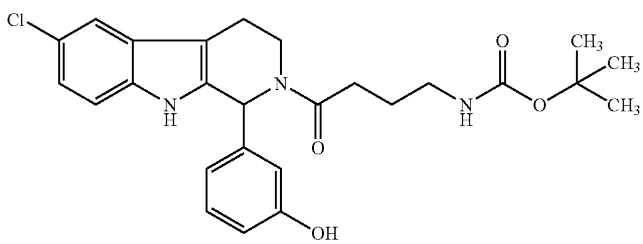 | tert-butyl 4-[6-chloro-1-(3-hydroxyphenyl)-1,3,4,9-tetrahydro-2H-beta-carbolin-2-yl]-4-oxobutylcarbamate | 484.9 |
| 28 | 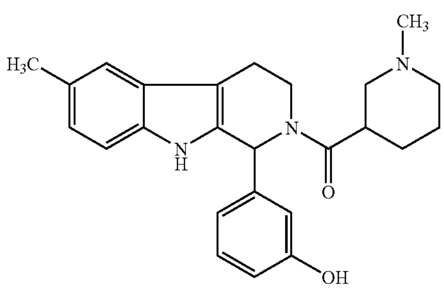 | 3-{6-methyl-2-[(1-methylpiperidin-3-yl)carbonyl]-2,3,4,9-tetrahydro-1H-beta-carbolin-1-yl}phenol | 404.5 |

TABLE 1-continued

Representative Tetrahydrocarboline Compounds.

| Compound | Structure | Name | MH+ |
|---|---|---|---|
| 29 | 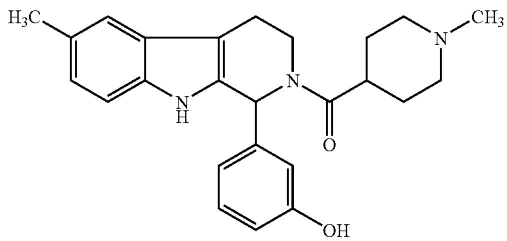 | 3-{6-methyl-2-[(1-methylpiperidin-4-yl)carbonyl]-2,3,4,9-tetrahydro-1H-beta-carbolin-1-yl}phenol | 404.5 |
| 30 | 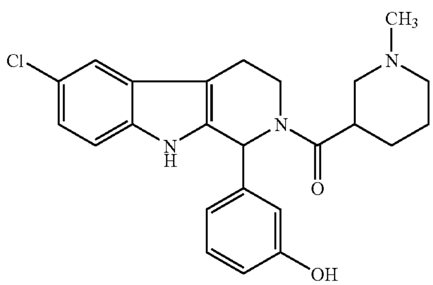 | 3-{6-chloro-2-[(1-methylpiperidin-3-yl)carbonyl]-2,3,4,9-tetrahydro-1H-beta-carbolin-1-yl}phenol | 424.9 |
| 31 | 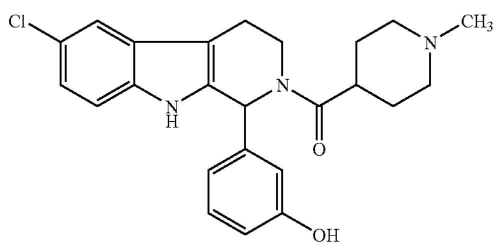 | 3-{6-chloro-2-[(1-methylpiperidin-4-yl)carbonyl]-2,3,4,9-tetrahydro-1H-beta-carbolin-1-yl}phenol | 424.9 |
| 32 | 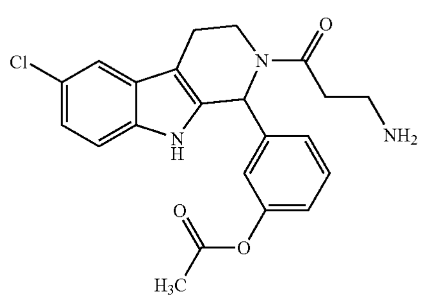 | 3-(2-beta-alanyl-6-chloro-2,3,4,9-tetrahydro-1H-beta-carboiin-1-yl)phenyl acetate | 412.1 |
| 33 | 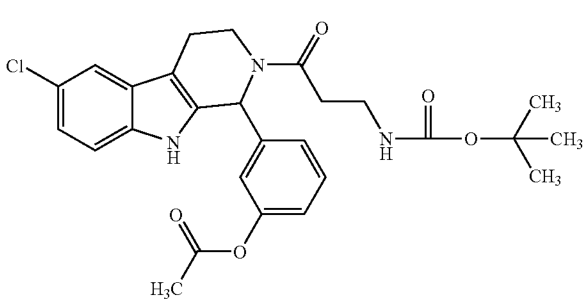 | 3-{2-[N-(tert-butoxycarbonyl)-beta-alanyl]-6-chloro-2,3,4,9-tetrahydro-1H-beta-carbolin-1-yl}phenyl acetate | 512.2 |

TABLE 1-continued

Representative Tetrahydrocarboline Compounds.

| Compound | Structure | Name | MH+ |
|---|---|---|---|
| 34 | 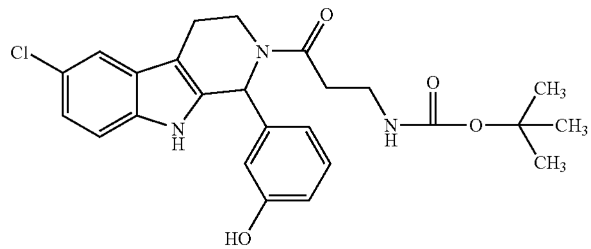 | 3-{2-[N-(tert-butoxycarbonyl)-beta-alanyl]-6-chloro-2,3,4,9-tetrahydro-1H-beta-carbolin-1-yl}phenol | 470.2 |
| 35 | 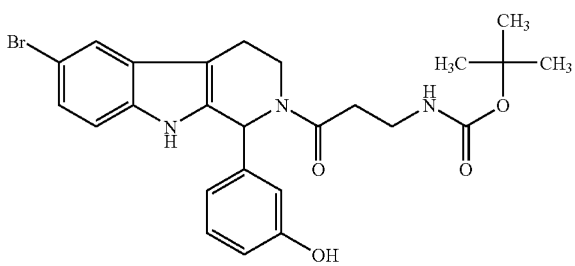 | 3-{2-[N-(tert-butoxycarbonyl)-beta-alanyl]-6-bromo-2,3,4,9-tetrahydro-1H-beta-carbolin-1-yl}phenol | 515.4 |
| 36 | 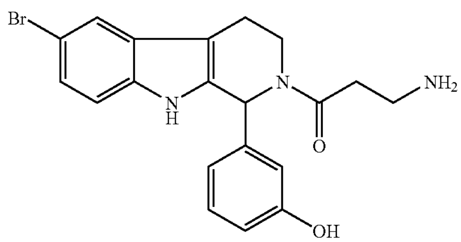 | 3-(2-beta-alanyl-6-bromo-2,3,4,9-tetrahydro-1H-beta-carbolin-1-yl)phenol | 415.2 |
| 37 | 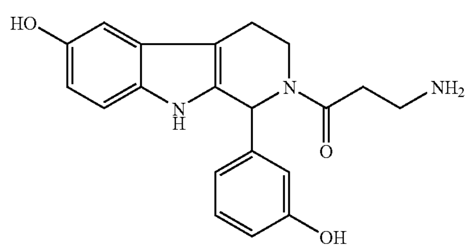 | 2-beta-alanyl-1-(3-hydroxyphenyl)-2,3,4,9-tetrahydro-1H-beta-carbolin-6-ol | 352.4 |
| 38 | 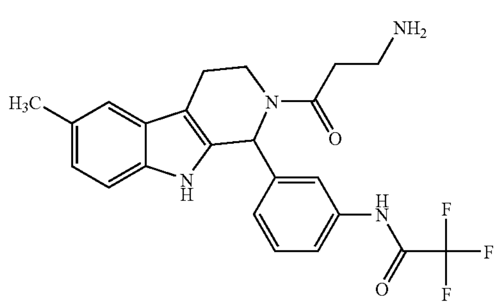 | N-[3-(2-beta-alanyl-6-methyl-2,3,4,9-tetrahydro-1H-beta-carbolin-1-yl)phenyl]-2,2,2-trifluoroacetamide | 445.5 |

TABLE 1-continued

Representative Tetrahydrocarboline Compounds.

| Compound | Structure | Name | MH+ |
|---|---|---|---|
| 39 | 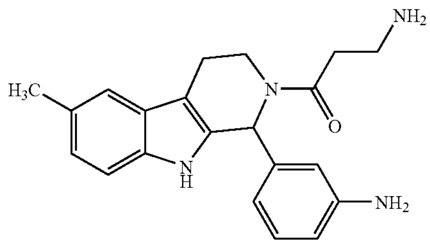 | 3-[1-(3-aminophenyl)-6-methyl-1,3,4,9-tetrahydro-2H-beta-carbolin-2-yl]-3-oxopropylamine | 349.5 |
| 40 | 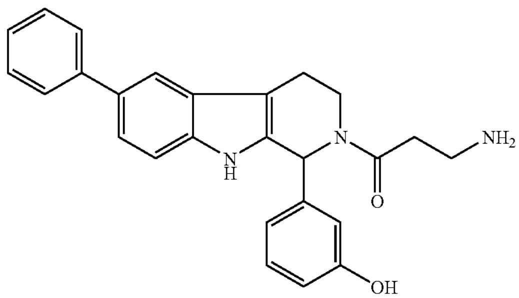 | 3-(2-beta-alanyl-6-phenyl-2,3,4,9-tetrahydro-1H-beta-carbolin-1-yl)phenol | 412.3 |
| 41 | 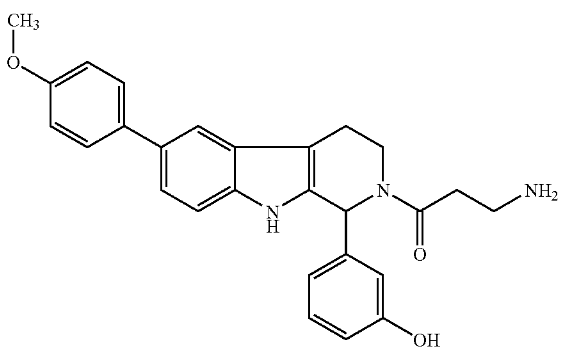 | 3-[2-beta-alanyl-6-(4-methoxyphenyl)-2,3,4,9-tetrahydro-1H-beta-carbolin-1-yl]phenol | 442.4 |
| 42 | 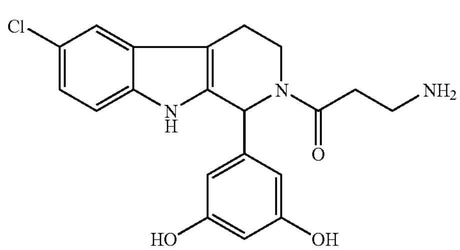 | 5-(2-beta-alanyl-6-chloro-2,3,4,9-tetrahydro-1H-beta-carbolin-1-yl)benzene-1,3-diol | 386.3 |
| 43 | 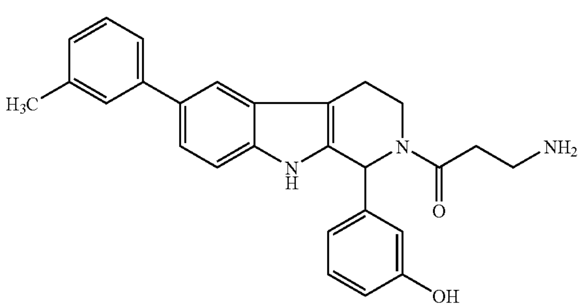 | 3-[2-beta-alanyl-6-(3-methylphenyl)-2,3,4,9-tetrahydro-1H-beta-carbolin-1-yl]phenol | 426.4 |

TABLE 1-continued

Representative Tetrahydrocarboline Compounds.

| Compound | Structure | Name | MH+ |
|---|---|---|---|
| 44 | 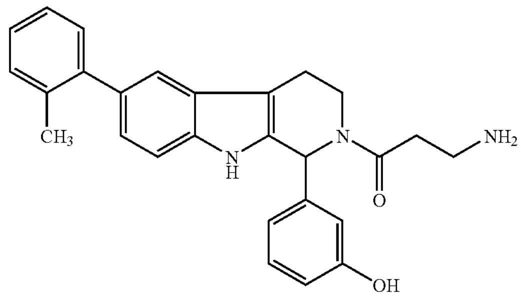 | 3-[2-beta-alanyl-6-(2-methylphenyl)-2,3,4,9-tetrahydro-1H-beta-carbolin-1-yl]phenol | 426.4 |
| 45 | 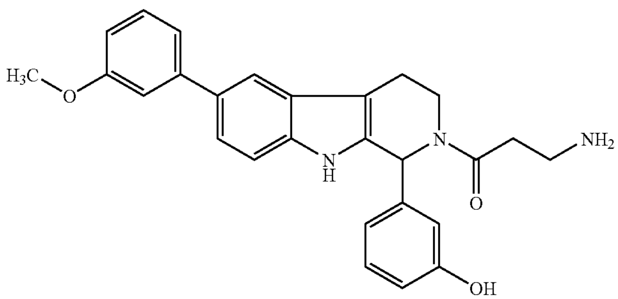 | 3-[2-beta-alanyl-6-(3-methoxyphenyl)-2,3,4,9-tetrahydro-1H-beta-carbolin-1-yl]phenol | 442.4 |
| 46 | 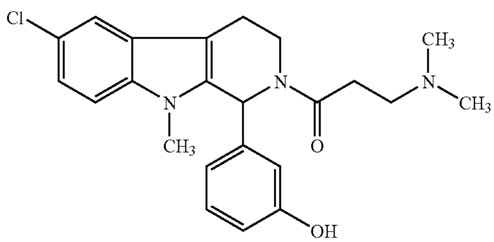 | 3-[6-chloro-2-(N,N-dimethyl-beta-alanyl)-9-methyl-2,3,4,9-tetrahydro-1H-beta-carbolin-1-yl]phenol | 412.2 |
| 47 | 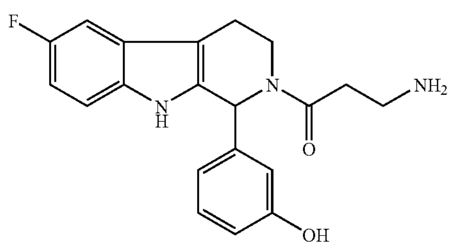 | 3-(2-beta-alanyl-6-fluoro-2,3,4,9-tetrahydro-1H-beta-carbolin-1-yl)phenol | 354 |
| 48 | 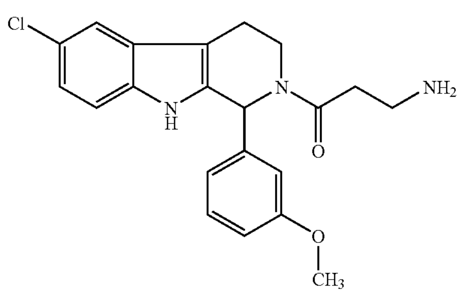 | 3-[6-chloro-1-(3-methoxyphenyl)-1,3,4,9-tetrahydro-2H-beta-carbolin-2-yl]-3-oxopropan-1-amine | 384 |

TABLE 1-continued

Representative Tetrahydrocarboline Compounds.

| Compound | Structure | Name | MH+ |
|---|---|---|---|
| 49 | 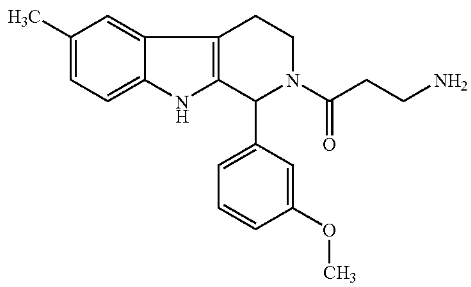 | 3-[1-(3-methoxyphenyl)-6-methyl-1,3,4,9-tetrahydro-2H-beta-carbolin-2-yl]-3-oxopropan-1-amine | 364 |
| 50 | 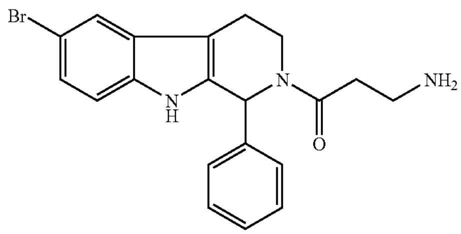 | 3-(6-bromo-1-phenyl-1,3,4,9-tetrahydro-2H-beta-carbolin-2-yl)-3-oxopropan-1-amine | 398.2 |
| 51 | 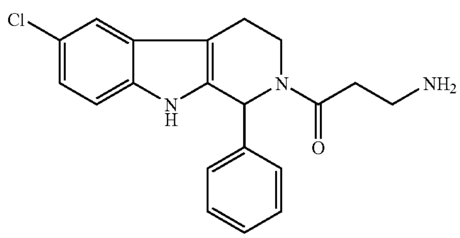 | 3-(6-chloro-1-phenyl-1,3,4,9-tetrahydro-2H-beta-carbolin-2-yl)-3-oxopropan-1-amine | 354.3 |
| 52 | 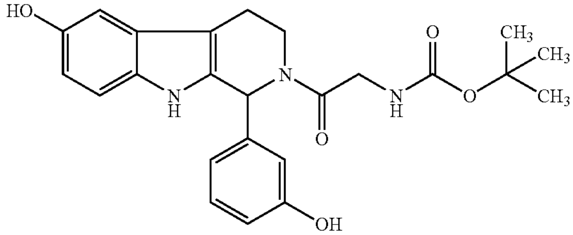 | 2-[N-(tert-butoxycarbonyl)-glycyl]-3-(hydroxyphenyl)-2,3,4,9-tetrahydro-1H-beta-carbolin-6-ol | 438.49 |
| 53 | 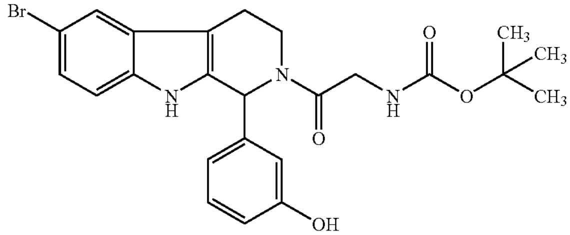 | 3-{6-bromo-2-[N-(tert-butoxycarbonyl)-glycyl]-2,3,4,9-tetrahydro-1H-beta-carbolin-1-yl}phenol | 500.11 |
| 54 | 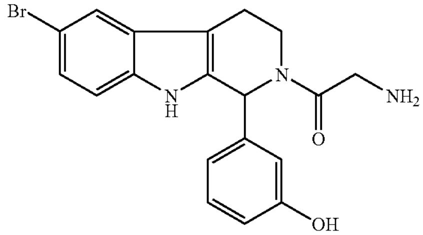 | 3-(6-bromo-2-glycyl-2,3,4,9-tetrahydro-1H-beta-carbolin-1-yl)phenol | 400.06 |

TABLE 1-continued

Representative Tetrahydrocarboline Compounds.

| Compound | Structure | Name | MH+ |
|---|---|---|---|
| 55 | 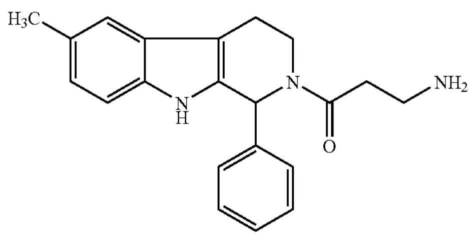 | 3-(6-methyl-1-phenyl-1,3,4,9-tetrahydro-2H-beta-carbolin-2-yl)-3-oxopropan-1-amine | 334.2 |
| 56 | 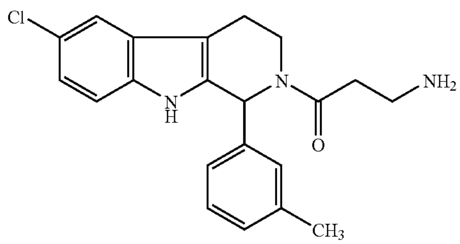 | 3-(6-chloro-1-(3-methylphenyl)-1,3,4,9-tetrahydro-2H-beta-carbolin-2-yl]-3-oxopropan-1-amine | 370 |
| 57 | 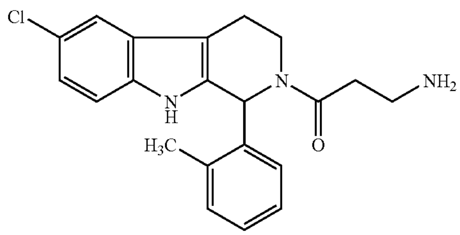 | 3-[6-chloro-1-(2-methylphenyl)-1,3,4,9-tetrahydro-2H-beta-carbolin-2-yl]-3-oxopropan-1-amine | 368 |
| 58 | 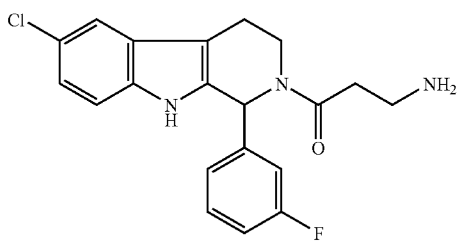 | 3-[6-chloro-1-(3-fluorophenyl)-1,3,4,9-tetrahydro-2H-beta-carbolin-2-yl]-3-oxopropan-1-amine | 372 |
| 69 | 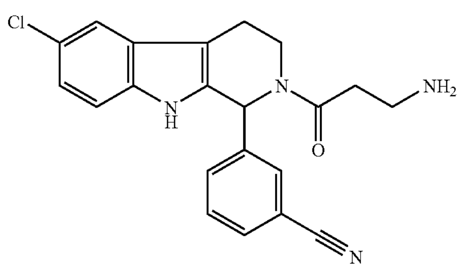 | 3-(2-beta-alanyl-6-chloro-2,3,4,9-tetrahydro-1H-beta-carbolin-1-yl)benzonitrile | 379 |
| 60 | 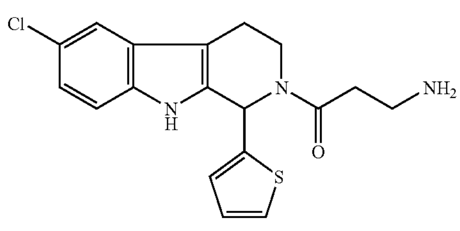 | 3-(6-chloro-1-thien-2-yl-1,3,4,9-tetrahydro-2H-beta-carbolin-2-yl)-3-oxopropan-1-amine | 360 |

TABLE 1-continued

Representative Tetrahydrocarboline Compounds.

| Compound | Structure | Name | MH+ |
|---|---|---|---|
| 61 | 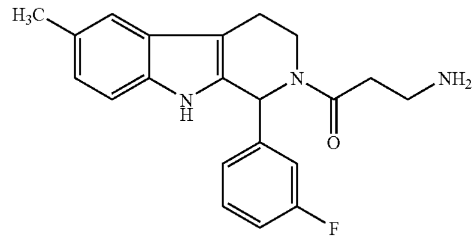 | 3-[1-(3-fluorophenyl)-6-methyl-1,3,4,9-tetrahydro-2H-beta-carbolin-2-yl]-3-oxopropan-1-amine | 352 |
| 62 | 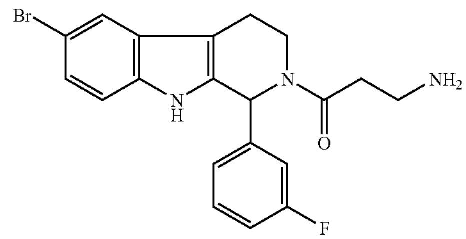 | 3-[6-bromo-1-(3-fluorophenyl)-1,3,4,9-tetrahydro-2H-beta-carbolin-2-yl]-3-oxopropan-1-amine | 418 |
| 63 | 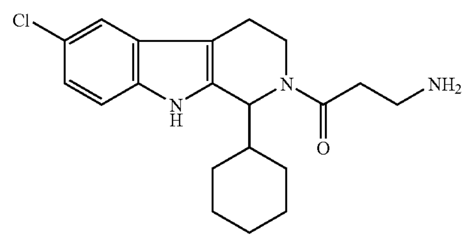 | 3-(6-chloro-1-cyclohexyl-1,3,4,9-tetrahydro-2H-beta-carbolin-2-yl)-3-oxopropan-1-amine | 360 |
| 64 | 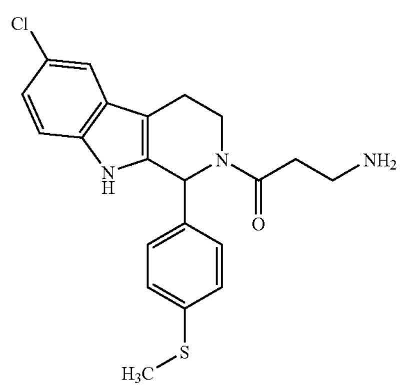 | 3-{6-chloro-1-[4-(methylthio)phenyl]-1,3,4,9-ttetrahydro-2H-beta-carbolin-2-yl}-3-oxopropan-1-amine | 401 |
| 65 | 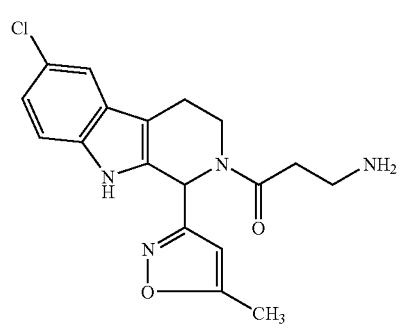 | 3-[6-chloro-1-(5-methylisoxazol-3-yl)-1,3,4,9-tetrahydro-2H-beta-carbolin-2-yl]-3-oxopropan-1-amine | 360 |

TABLE 1-continued

Representative Tetrahydrocarboline Compounds.

| Compound | Structure | Name | MH+ |
|---|---|---|---|
| 66 | 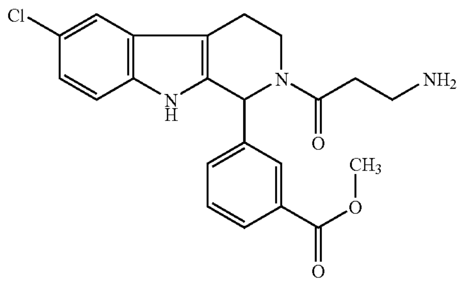 | methyl 3-(2-beta-alanyl-6-chloro-2,3,4,9-tetrahydro-1H-beta-carbolin-1-yl)benzoate | 412 |
| 67 | 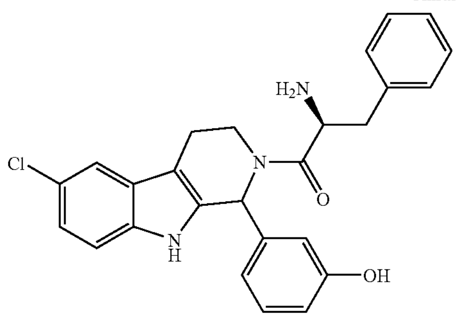 | 3-(6-chloro-2-L-phenylalanyl-2,3,4,9-tetrahydro-1H-beta-carbolin-1-yl)phenol | 446.3 |
| 68 | 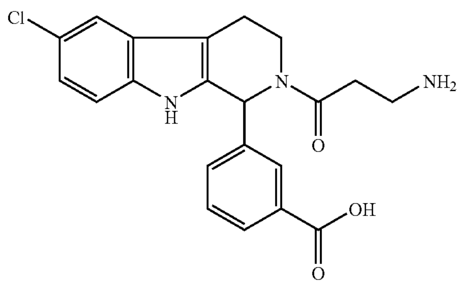 | 3-(2-beta-alanyl-6-chloro-2,3,4,9-tetrahydro-1H-beta-carbolin-1-yl)benzoic acid | 398 |
| 69 | 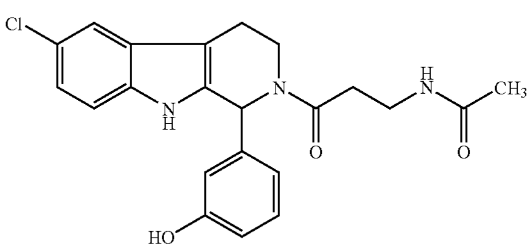 | 3-[2-(N-acetyl-beta-alanyl)-6-chloro-2,3,4,9-tetrahydro-1H-beta-carbolin-1-yl]phenol | 412.1 |
| 70 | 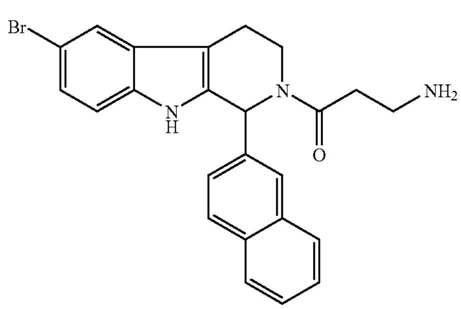 | 3-[6-bromo-1-(2-naphthyl)-1,3,4,9-tetrahydro-2H-beta-carbolin-2-yl]-3-oxopropan-1-amine | 449 |

TABLE 1-continued

Representative Tetrahydrocarboline Compounds.

| Compound | Structure | Name | MH+ |
|---|---|---|---|
| 71 | 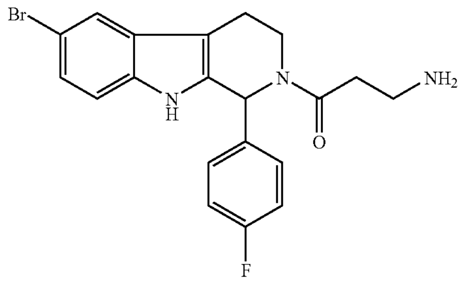 | 3-[6-bromo-1-(4-fluorophenyl)-1,3,4,9-tetrahydro-2H-beta-carbolin-2-yl]-3-oxopropan-1-amine | 417 |
| 72 | 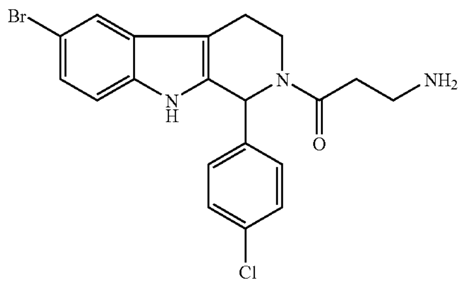 | 3-[6-bromo-1-(4-chlorophenyl)-1,3,4,9-tetrahydro-2H-beta-carbolin-2-yl]-3-oxopropan-1-amine | 434 |
| 73 | 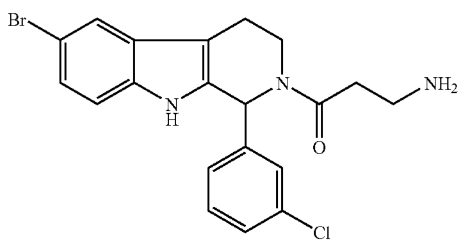 | 3-[6-bromo-1-(3-chlorophenyl)-1,3,4,9-tetrahydro-2H-beta-carbolin-2-yl]-3-oxopropan-1-amine | 434 |
| 74 | 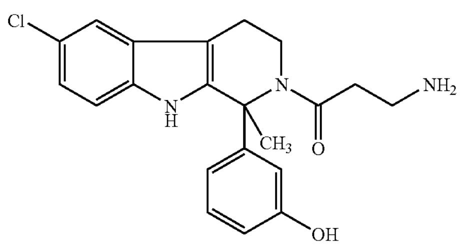 | 3-(2-beta-alanyl-6-chloro-1-methyl-2,3,4,9-tetrahydro-1H-beta-carbolin-1-yl)phenol | 384.4 |
| 75 | 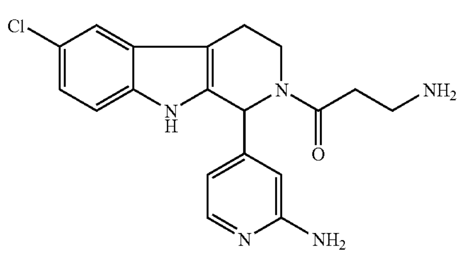 | 4-[2-(3-aminopropanoyl)-6-chloro-2,3,4,9-tetrahydro-1H-beta-carbolin-1-yl]pyridin-2-amine | 370.3 |

TABLE 1-continued

Representative Tetrahydrocarboline Compounds.

| Compound | Structure | Name | MH+ |
|---|---|---|---|
| 76 | 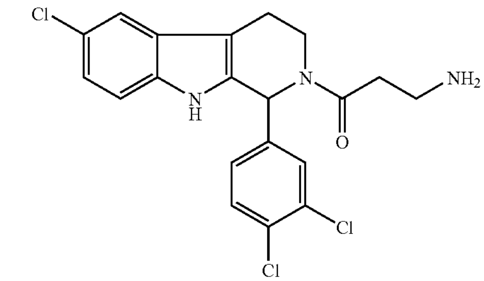 | 3-[6-chloro-1-(3,4-dichlorophenyl)-1,3,4,9-tetrahydro-2H-beta-carbolin-2-yl]-3-oxopropan-1-amine | 423 |
| 77 | 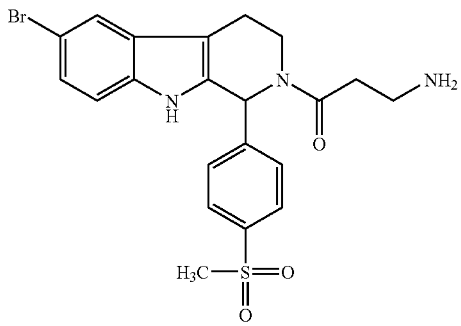 | 3-{6-bromo-1-[4-(methylsulfonyl)phenyl]-1,3,4,9-ttetrahydro-2H-beta-carbolin-2-yl}-3-oxopropan-1-amine | 477 |
| 78 | 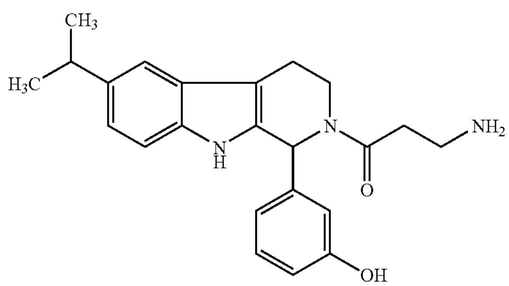 | 3-(2-beta-alanyl-6-isopropyl-2,3,4,9-tetrahydro-1H-beta-carbolin-1-yl)phenol | 378.2 |
| 79 | 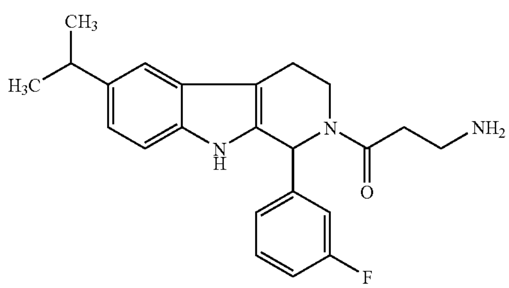 | 2-[1-(3-fluorophenyl)-6-isopropyl-1,3,4,9-ttetrahydro-2H-beta-carbolin-2-yl]-3-oxopropan-1-amine | 380.2 |
| 80 | 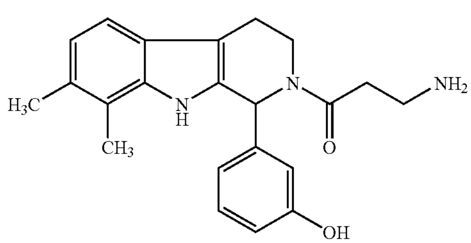 | 3-(2-beta-alanyl-7,8-dimethyl-2,3,4,9-tetrahydro-1H-beta-carbolin-1-yl)phenol | 364.2 |

TABLE 1-continued

Representative Tetrahydrocarboline Compounds.

| Compound | Structure | Name | MH+ |
|---|---|---|---|
| 81 | 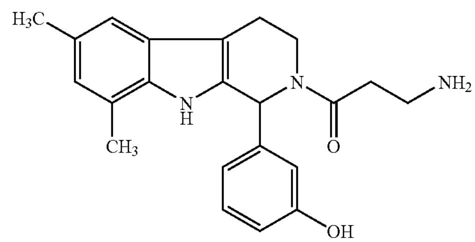 | 3-(2-beta-alanyl-6,8-dimethyl-2,3,4,9-tetrahydro-1H-beta-carbolin-1-yl)phenol | 364.2 |
| 82 | 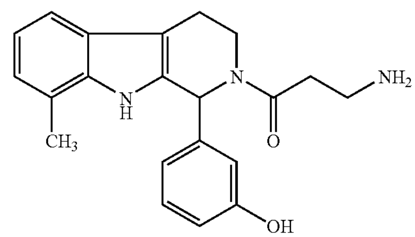 | 3-(2-beta-alanyl-8-methyl-2,3,4,9-tetrahydro-1H-beta-carbolin-1-yl)phenol | 350.2 |
| 83 | 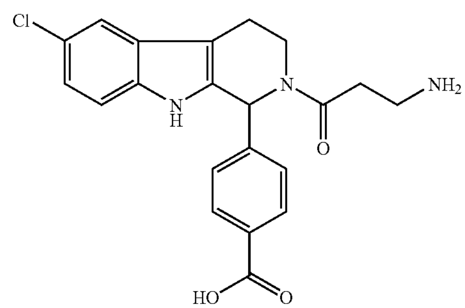 | 4-(2-beta-alanyl-6-chloro-2,3,4,9-tetrahydro-1H-beta-carbolin-1-yl)benzoic acid | 398 |
| 84 | 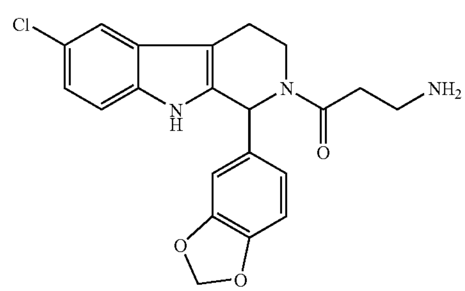 | 3-[1-(1,3-benzodioxol-5-yl)-6-chloro-1,3,4,9-tetrahydro-2H-beta-carbolin-2-yl]-3-oxopropan-1-amine | 398 |
| 85 | 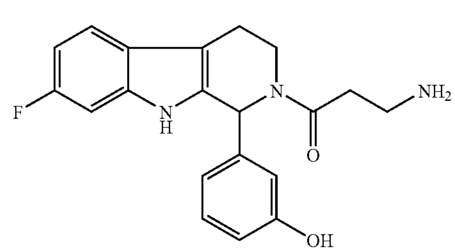 | 3-(2-beta-alanyl-7-fluoro-2,3,4,9-tetrahydro-1H-beta-carbolin-1-yl)phenol | 354.3 |

TABLE 1-continued

Representative Tetrahydrocarboline Compounds.

| Compound | Structure | Name | MH+ |
|---|---|---|---|
| 86 | 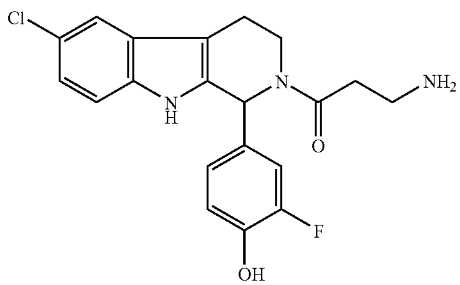 | 4-(2-beta-alanyl-6-chloro-2,3,4,9-tetrahydro-1H-beta-carbolin-1-yl)-2-fluorophenol | 388.3 |
| 87 | 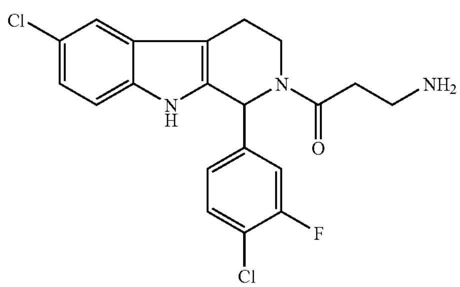 | 3-[6-chloro-1-(4-chloro-3-fluorophenyl)-1,3,4,9-tetrahydro-2H-beta-carbolin-2-yl]-3-oxopropan-1-amine | 406 |
| 88 | 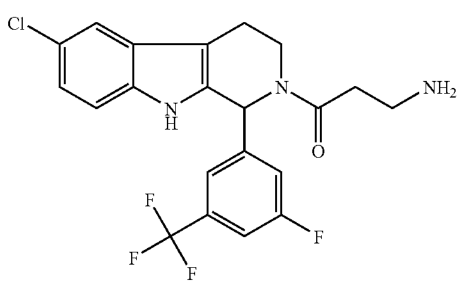 | 3-{6-chloro-1-[3-fluoro-5-(trifluoromethyl)phenyl]-1,3,4,9-tetrahydro-2H-beta-carbolin-2-yl}-3-oxopropan-1-amine | 440 |
| 89 | 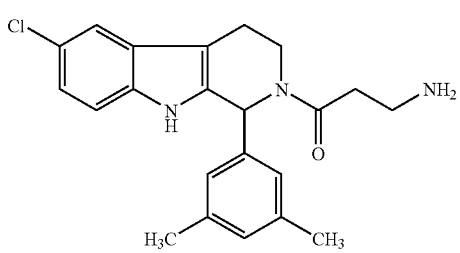 | 3-[6-chloro-1-(3,5-dimethylphenyl)-1,3,4,9-tetrahydro-2H-beta-carbolin-2-yl]-3-oxopropan-1-amine | 382 |
| 90 | 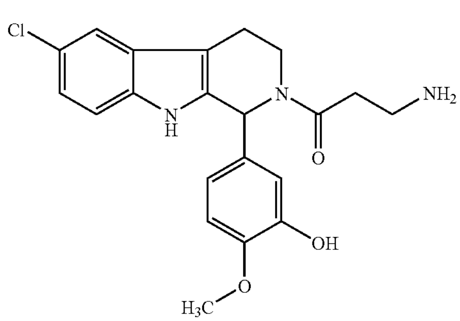 | 5-(2-beta-alanyl-6-chloro-2,3,4,9-tetrahydro-1H-beta-carbolin-1-yl)-2-methoxyphenol | 400 |

TABLE 1-continued

Representative Tetrahydrocarboline Compounds.

| Compound | Structure | Name | MH+ |
|---|---|---|---|
| 91 | 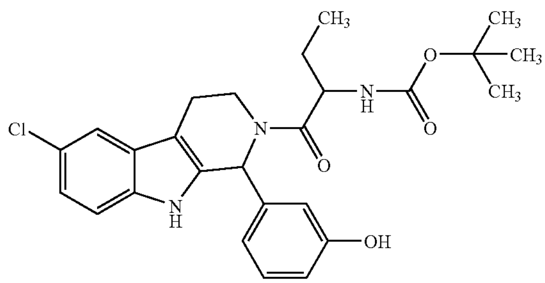 | tert-butyl 1-{[6-chloro-1-(3-hydroxyphenyl)-1,3,4,9-tetrahydro-2H-beta-carbolin-2-yl]carbonyl}propylcarbamate | 484.2 |
| 92 | 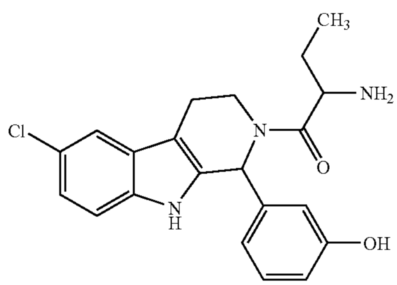 | 3-[2-(2-aminobutanoyl)-6-chloro-2,3,4,9-tetrahydro-1H-beta-oarbolin-1-yl]phenol | 384.3 |
| 93 | Chiral | tert-butyl (1R)-2-[6-chloro-1-(3-hydroxyphenyl)-1,3,4,9-tetrahydro-2H-beta-carbolin-2-yl]-2-oxo-1-phenylethylcarbamate | 532.4 |
| 94 | Chiral | 3-{2-[(2R)-2-amino-2-phenylethanoyl]-6-chloro-2,3,4,9-tetrahydro-1H-beta-carbolin-1-yl}phenol | 31.92 |

TABLE 1-continued

Representative Tetrahydrocarboline Compounds.

| Compound | Structure | Name | MH+ |
|---|---|---|---|
| 95 | 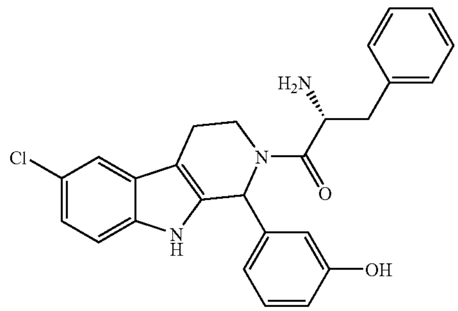 | 3-(6-chloro-2-D-phenylalanyl-2,3,4,9-tetrahydro-1H-beta-carbolin-1-yl)phenol | 446.3 |
| 96 | 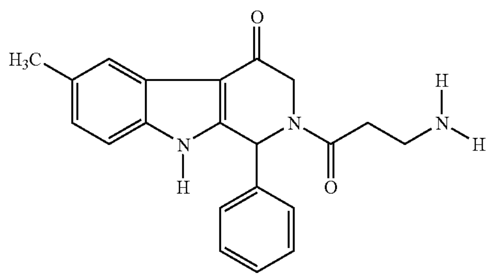 | 2-beta-alanyl-6-methyl-1-phenyl-1,2,3,9-tetrahydro-4H-beta-carbolin-4-one | 348.2 |
| 97 | 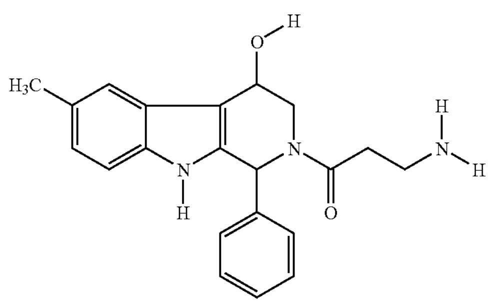 | 2-beta-alanyl-6-methyl-1-phenyl-2,3,4,9-tetrahydro-1H-beta-carbolin-4-ol | 350.2 |
| 98 | 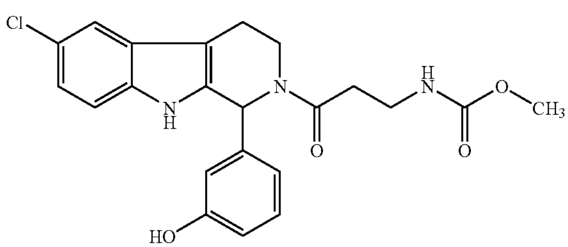 | methyl 3-[6-chloro-1-(3-hydroxyphenyl)-1,3,4,9-tetrahydro-2H-beta-carbolin-2-yl]-3-oxopropylcarbamate | 428.1 |
| 99 | 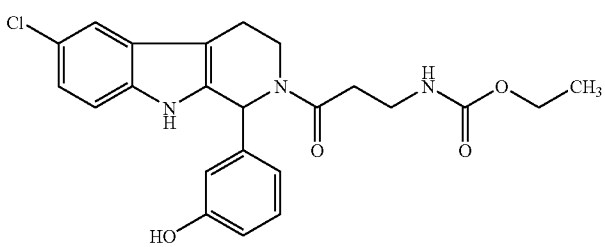 | ethyl 3-[6-chloro-1-(3-hydroxyphenyl)-1,3,4,9-tetrahydro-2H-beta-carbolin-2-yl]-3-oxopropylcarbamate | 442.1 |

TABLE 1-continued

Representative Tetrahydrocarboline Compounds.

| Compound | Structure | Name | MH+ |
|---|---|---|---|
| 100 | 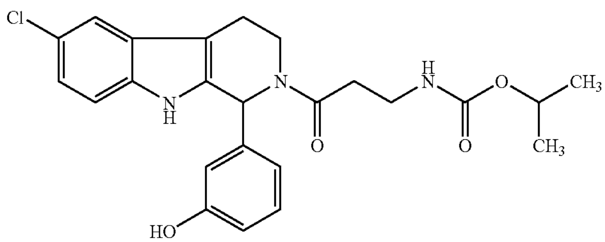 | isopropyl 3-[6-chloro-1-(3-hydroxyphenyl)-1,3,4,9-tetrahydro-2H-beta-carbolin-2-yl]-3-oxopropylcarbamate | 456.2 |
| 101 | 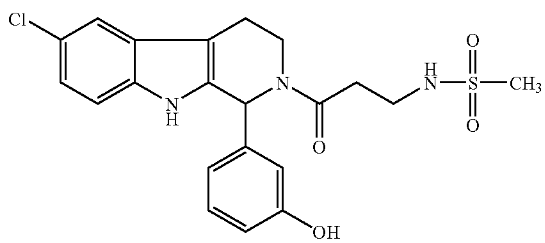 | N-{[6-chloro-1-(3-hydroxyphenyl)-1,3,4,9-ttetrahydro-2H-beta-carbolin-2-yl]-3-oxopropyl}methanesulfonamide | 448.1 |
| 102 | 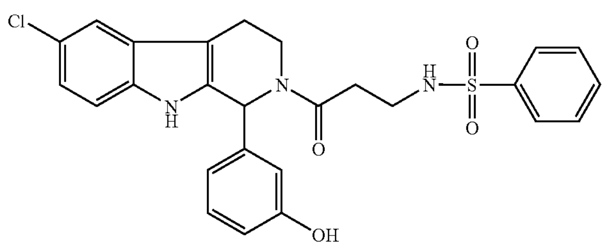 | N-{3-[6-chloro-1-(3-hydroxyphenyl)-1,3,4,9-tetrahydro-2H-beta-carbolin-2-yl]-3-oxopropyl}benzenesulfonamide | 510.1 |
| 103 | 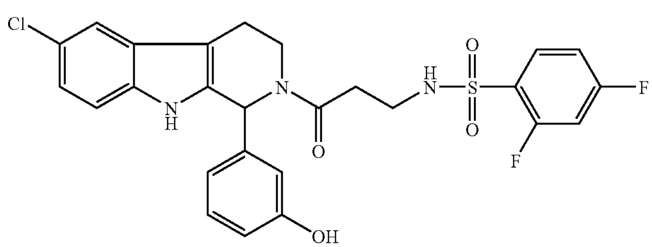 | N-{3-[6-chloro-1-(3-hydroxyphenyl)-1,3,4,9-tetrahydro-2H-beta-carbolin-2-yl]-3-oxopropyl}-2,4-difluorobenzenesulfonamide | 546.1 |
| 104 | 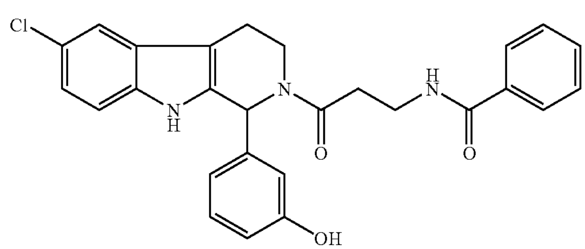 | N-{3-[6-chloro-1-(3-hydroxyphenyl)-1,3,4,9-ttetrahydro-2H-beta-carbolin-2-yl]-3-oxopropyl}benzamide | 474.2 |
| 105 | 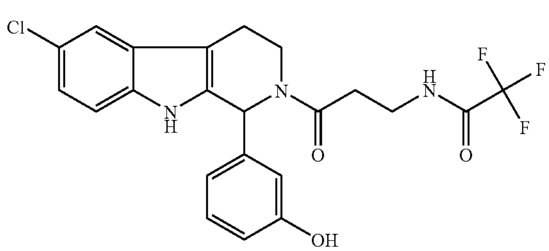 | N-{3-[6-chloro-1-(3-hydroxyphenyl)-1,3,4,9-ttetrahydro-2H-beta-carbolin-2-yl]-3-oxopropyl}-2,2,2-trifluoroacetamide | 466.1 |

TABLE 1-continued

Representative Tetrahydrocarboline Compounds.

| Compound | Structure | Name | MH+ |
|---|---|---|---|
| 106 | 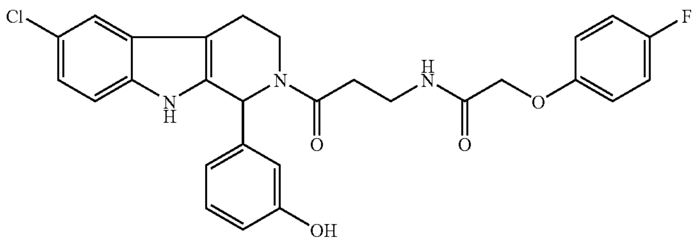 | N-{3-[6-chloro-1-(3-hydroxyphenyl)-1,3,4,9-ttetrahydro-2H-beta-carbolin-2-yl]-3-oxopropyl}-2-(4-fluorophenoxy)acetamide | 522.2 |
| 107 | 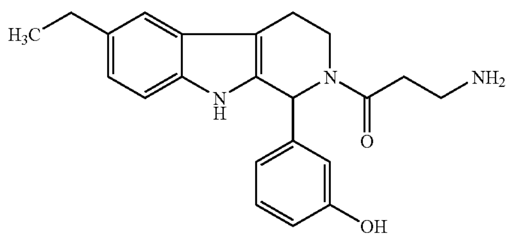 | 3-[2-(3-aminopropanoyl)-6-ethyl-2,3,4,9-tetrahydro-1H-beta-carbolin-1-yl]phenol | 363.2 |
| 108 | 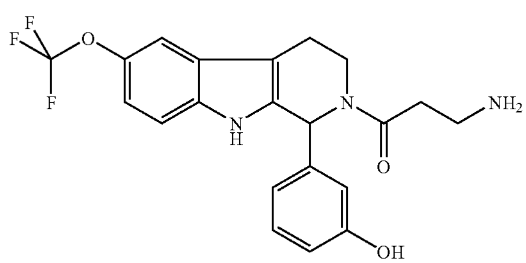 | 3-[2-(3-aminopropanoyl)-6-(trifluoromethoxy)-2,3,4,9-tetrahydro-1H-beta-carbolin-1-yl]phenol | 419.2 |
| 109 | 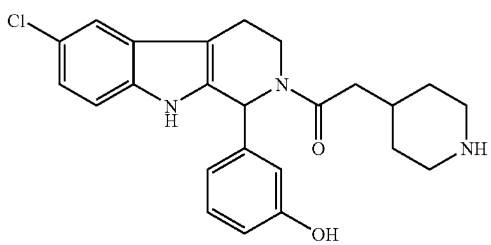 | 3-[6-chloro-2-(piperidin-4-ylacetyl)-2,3,4,9-ttetrahydro-1H-beta-carbolin-1-yl]phenol | 423.2 |
| 110 | 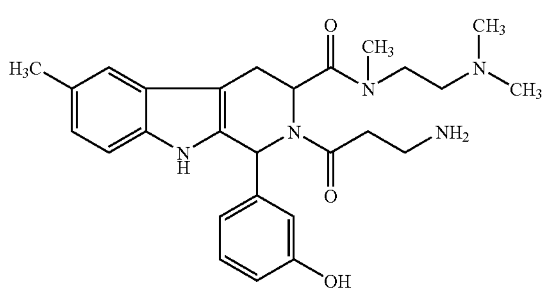 | 2-(3-aminopropanoyl)-N-[2-(dimethylamino)ethyl]-1-(3-hydroxyphenyl)-N,6-dimethyl-2,3,4,9-tetrahydro-1H-beta-carboline-3-carboxamide | 478.6 |

TABLE 1-continued

Representative Tetrahydrocarboline Compounds.

| Compound | Structure | Name | MH+ |
|---|---|---|---|
| 111 | 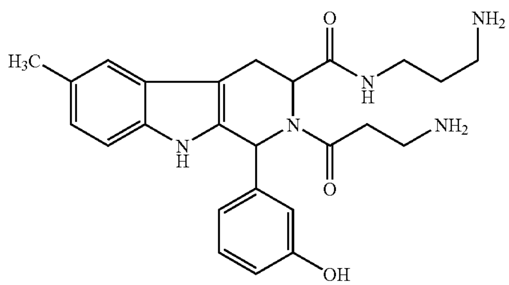 | 2-(3-aminopropanoyl)-N-(3-aminopropyl)-1-(3-hydroxyphenyl)-6-methyl-2,3,4,9-tetrahydro-1H-beta-carboline-3-carboxamide | 449.55 |
| 112 | 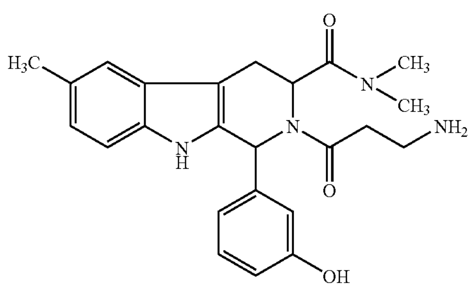 | 2-(3-aminopropanoyl)-1-(3-hydroxyphenyl)-N,N,6-trimethyl-2,3,4,9-tetrahydro-1H-beta-carboline-3-carboxamide | 420.51 |
| 113 | 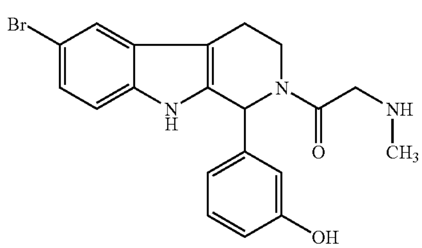 | 3-{6-bromo-2-[(methylamino)acetyl]-2,3,4,9-tetrahydro-1H-beta-carbolin-1-yl}phenol | 416.2 |
| 114 | 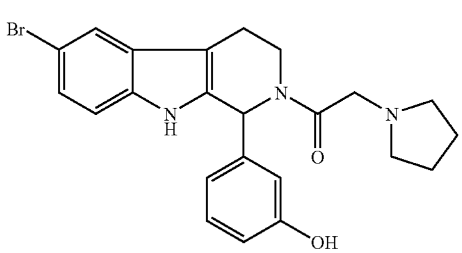 | 3-[6-bromo-2-(pyrrolidin-1-ylacetyl)-2,3,4,9-tetrahydro-1H-beta-carbolin-1-yl]phenol | 456.3 |
| 115 | 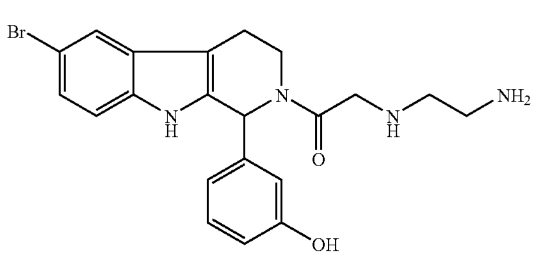 | 3-(2-{[(2-aminoethyl)amino]acetyl}-6-bromo-2,3,4,9-tetrahydro-1H-beta-carbolin-1-yl)phenol | 445.2 |

TABLE 1-continued

Representative Tetrahydrocarboline Compounds.

| Compound | Structure | Name | MH+ |
|---|---|---|---|
| 116 | 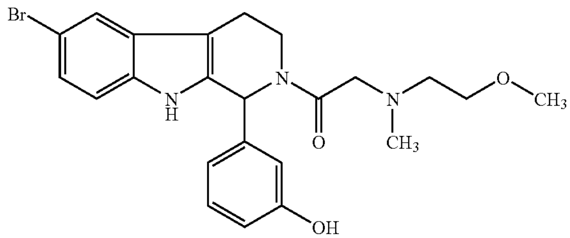 | 3-(6-bromo-2-{[(2-methoxyethyl)(methyl)amino]acetyl}-2,3,4,9-ttetrahydro-1H-beta-carbolin-1-yl)phenol | 414.3 |
| 117 | 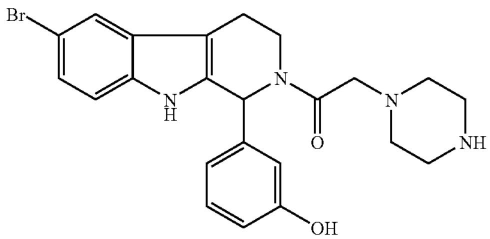 | 3-[6-bromo-2-(piperazin-1-ylacetyl)-2,3,4,9-tetrahydro-1H-beta-carbolin-1-yl]phenol | 471.2 |
| 118 | 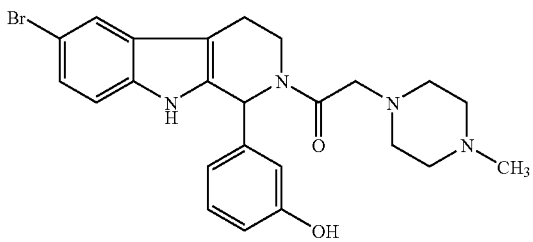 | 3-{6-bromo-2-[(4-methylpiperazin-1-yl)acetyl]-2,3,4,9-tetrahydro-1H-beta-carbolin-1-yl}phenol | 485.3 |
| 119 | 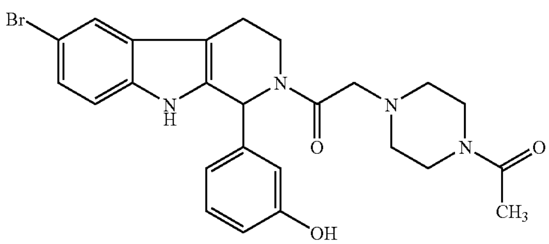 | 3-{2-[(4-acetylpiperazin-1-yl)acetyl]-6-bromo-2,3,4,9-tetrahydro-1H-beta-carbolin-1-yl}phenol | 513.3 |
| 120 | 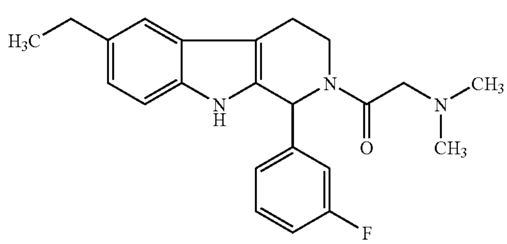 | N-{2-[6-ethyl-1-(3-fluorophenyl)-1,3,4,9-tetrahydro-2H-beta-carbolin-2-yl]-2-oxoethyl}-N,N-dimethylamine | 379.2 |
| 121 | 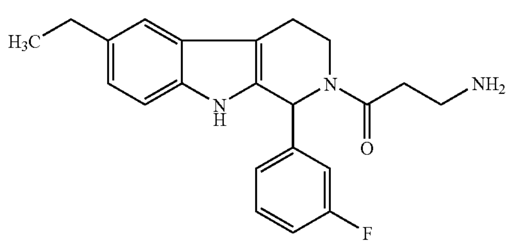 | 3-[6-ethyl-1-(3-fluorophenyl)-1,3,4,9-tetrahydro-2H-beta-carbolin-2-yl]-3-oxopropan-1-amine | 365.2 |

TABLE 1-continued

Representative Tetrahydrocarboline Compounds.

| Compound | Structure | Name | MH+ |
|---|---|---|---|
| 122 | 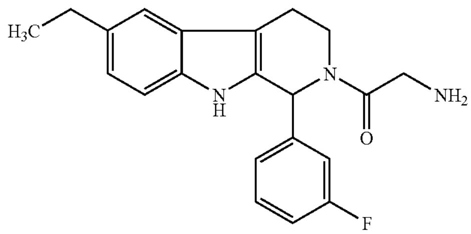 | 2-[6-ethyl-1-(3-fluorophenyl)-1,3,4,9-tetrahydro-2H-beta-carbolin-2-yl]-2-oxoethanamine | 351.2 |
| 123 | 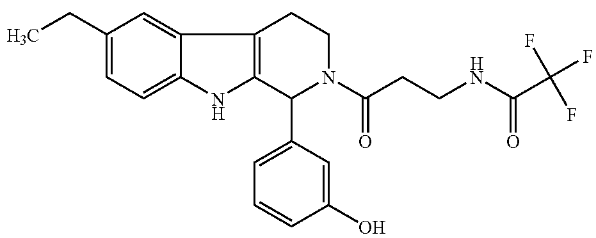 | N-{3-[6-ethyl-1-(3-hydroxyphenyl)-1,3,4,9-tetrahydro-2H-beta-carbolin-2-yl]-3-oxopropyl}-2,2,2-trifluoroacetamide | 459.2 |
| 124 | 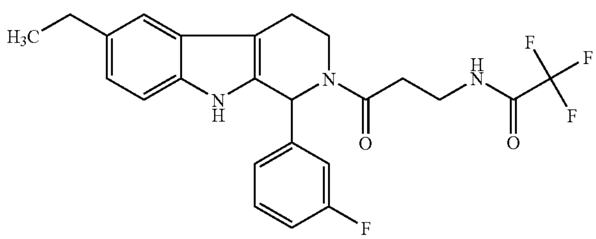 | N-{3-[6-ethyl-1-(3-fluorophenyl)-1,3,4,9-tetrahydro-2h-beta-carbolin-2-yl]-3-oxopropyl}-2,2,2-trifluoroacetamide | 461.2 |
| 125 | 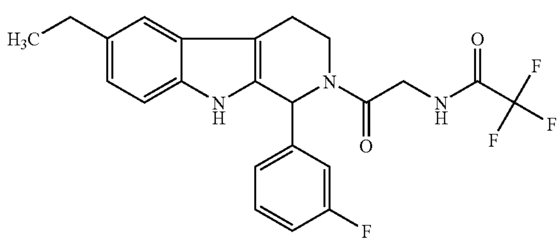 | N-{2-[6-ethyl-1-(3-fluorophenyl)-1,3,4,9-tetrahydro-2H-beta-carbolin-2-yl]-2-oxoethyl}-2,2,2-trifluoroacetamide | 447.2 |
| 126 | 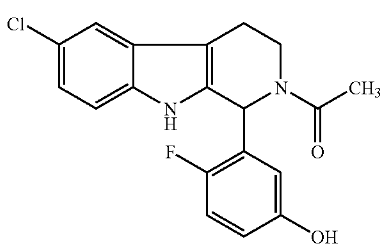 | 3-(2-acetyl-6-chloro-2,3,4,9-tetrahydro-1H-beta-carbolin-1-yl)-4-fluorophenol | 359.6 |
| 127 | 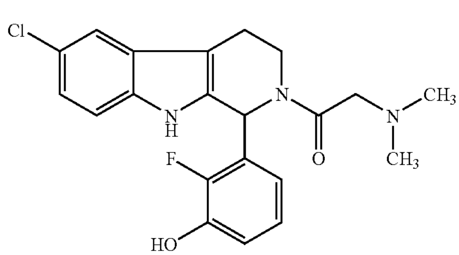 | 3-{6-chloro-2-[(dimethylamino)acetyl]-2,3,4,9-ttetrahydro-1H-beta-carbolin-1-yl}-2-fluorophenol | 402.1 |

TABLE 1-continued

Representative Tetrahydrocarboline Compounds.

| Compound | Structure | Name | MH+ |
|---|---|---|---|
| 128 | 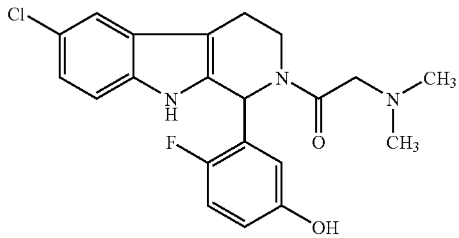 | 3-{6-chloro-2-[(dimethylamino)acetyl]-2,3,4,9-ttetrahydro-1H-beta-carbolin-1-yl}-4-fluorophenol | 402.1 |
| 129 | Chiral | tert-butyl (1R)-1-{[6-chloro-1-(3-hydroxyphenyl)-1,3,4,9-tetrahydro-2H-beta-carbolin-2-yl]carbonyl}propylcarbamate | 484.2 |
| 130 | Chiral | 3-{2-[(2S)-2-amino-3-methylbutanoyl]-6-chloro-2,3,4,9-tetrahydro-1H-beta-carbolin-1-yl}phenol | 398.2 |
| 131 | Chiral | 3-{2-[(2R)-2-amino-3-methylbutanoyl]-6-chloro-2,3,4,9-ttetrahydro-1H-beta-carbolin-1-yl}phenol | 398.2 |
| 132 | Chiral | 3-{2-[(2R)-2-aminobutanoyl]-6-chloro-2,3,4,9-tetrahydro-1H-beta-carbolin-1-yl}phenol | 384.2 |

TABLE 1-continued

Representative Tetrahydrocarboline Compounds.

| Compound | Structure | Name | MH+ |
|---|---|---|---|
| 133 | 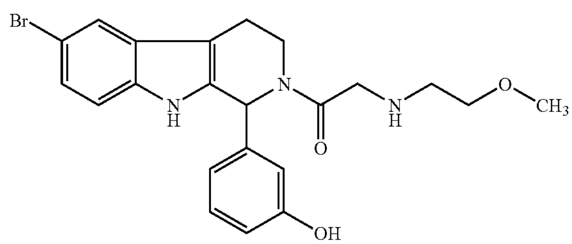 | 3-(6-bromo-2-{[(2-methoxyethyl)amino]acetyl}-2,3,4,9-tetrahydro-1H-beta-carbolin-1-yl)phenol | 460.0 |
| 134 | 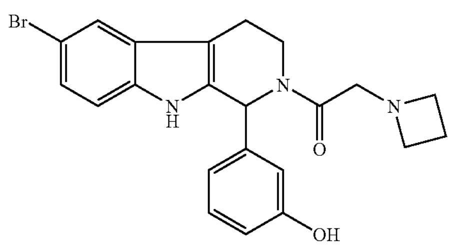 | 3-[2-(azetidin-1-ylacetyl)-6-bromo-2,3,4,9-tetrahydro-1H-beta-carbolin-1-yl]phenol | 442.0 |
| 135 | 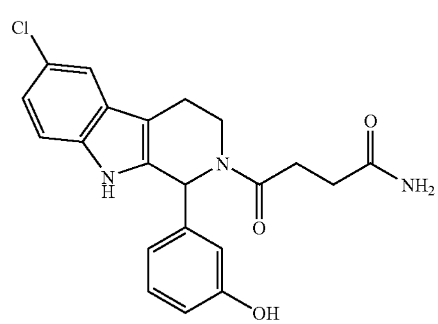 | 4-[6-chloro-1-(3-hydroxyphenyl)-1,3,4,9-tetrahydro-2H-beta-carbolin-2-yl]-4-oxobutanamide | 398.1 |
| 136 | 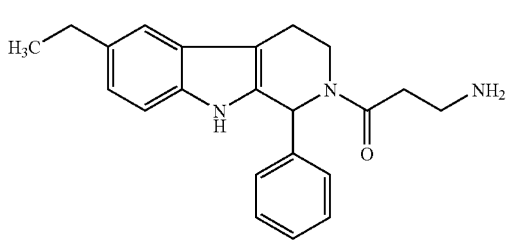 | 3-(6-ethyl-1-phenyl-1,3,4,9-tetrahydro-2H-beta-carbolin-2-yl)-3-oxopropan-1-amine | 347.2 |
| 137 | 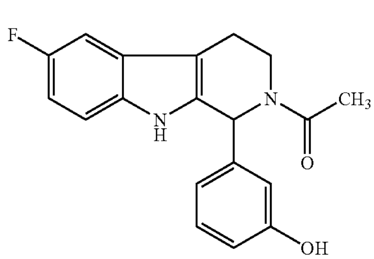 | 3-(2-acetyl-6-fluoro-2,3,4,9-tetrahydro-1H-beta-carbolin-1-yl)phenol | 325.1 |

TABLE 1-continued

Representative Tetrahydrocarboline Compounds.

| Compound | Structure | Name | MH+ |
|---|---|---|---|
| 138 | 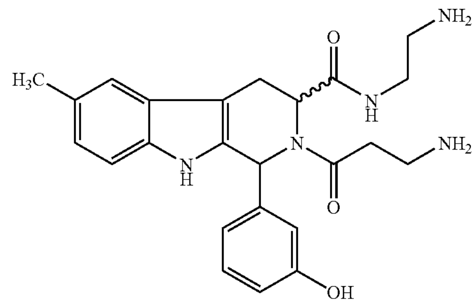 | N-(2-aminoethyl)-2-(3-aminopropanoyl)-1-(3-hydroxyphenyl)-6-methyl-2,3,4,9-tetrahydro-1H-beta-carboline-3-carboxamide | 435.52 |
| 139 | 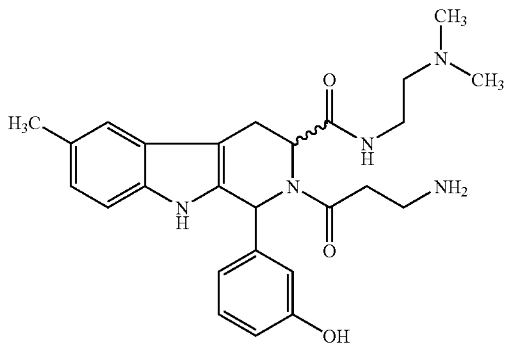 | 2-(3-aminopropanoyl)-N-[2-(dimethylamino)ethyl]-1-(3-hydroxyphenyl)-6-methyl-2,3,4,9-tetrahydro-1H-beta-carboline-3-carboxamide | 463.58 |

Using the procedure described in Example 13, the above compounds were shown to have an KSP inhibitory activity at an $IC_{50}$ of less than about 50 µM. Certain of the compounds have an $IC_{50}$ of less than about 1 µM, and certain others of the compounds have an $IC_{50}$ of less than about 100 nM.

Example 13

Assay for Determining KSP Activity

In this example, a representative in vitro assay for determining KSP activity is described.

Purified microtubules from bovine brain were purchased from Cytoskeleton Inc. The motor domain of human KSP (Eg5, KNSL1) was cloned and purified to a purity of greater than 95%. Biomol Green was purchased from Affinity Research Products Ltd.

Microtubules and the KSP motor protein were diluted in assay buffer (20 mM Tris-HCl, pH 7.5, 1 mM $MgCl_2$, 10 mM DTT and 0.25 mg/ml BSA) to a concentration of 35 ug/ml for microtubules and 45 nM for KSP. The microtubule/KSP mixture was then pre-incubated at 37° C. for 10 min to promote the binding of KSP to microtubules. ATP was also diluted to a concentration of 300 uM in the same assay buffer. To each well of the testing plate (384 well plate) containing 1.25 uL of compounds in DMSO or DMSO only, 25 uL of ATP solution. To start the reaction, 25 uL of microtubule/KSP solution was added to the ATP/compound mixture. The plates were incubated at room temperature for 1 hr. At the end of incubation period, 65 uL of Biomol Green was added to each well. The plates were incubated for 5-10 min and then the absorbance at 630 nm was determined. Biomol Green reagent is a malachite green based dye that detects the release of inorganic phosphate. Developed color signal was read using a Victor II reader. The concentration of each compound for 50% inhibition ($IC_{50}$) was calculated by nonlinear regression using either XLFit for Excel or Prism data analysis software by GraphPad Software Inc.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the formula (I):

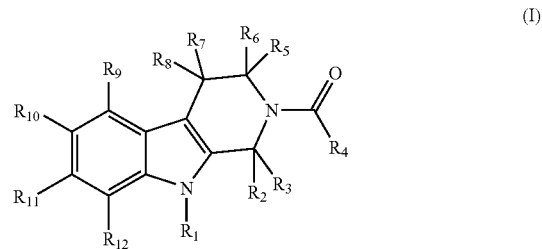

(I)

or a stereoisomer, tautomer, pharmaceutically acceptable salt, or ester thereof, wherein
$R_1$ is selected from the group consisting of
(1) hydrogen, and
(2) substituted or unsubstituted $C_1$-$C_6$ alkyl;
$R_2$ is substituted or unsubstituted aryl;
$R_3$ is hydrogen;

$R_4$ is a nitrogen-containing group, wherein the nitrogen-containing group is selected from the group consisting of amino alkyl, amine, cyclic amine, carbamate, amide, and sulfonamide groups;

$R_5$ is selected from the group consisting of
   (1) hydrogen,
   (2) $CO_2R_{5a}$, and
   (3) $CONR_{5b}R_{5c}$,
   wherein $R_{5a}$, $R_{5b}$, and $R_{5c}$ are selected from the group consisting of
      (a) substituted or unsubstituted alkyl, and
      (b) substituted or unsubstituted aryl;

$R_6$ is hydrogen;

$R_7$ is hydrogen or hydroxy;

$R_8$ is hydrogen, or $R_7$ and $R_8$ taken together with the carbon atom to which $R_7$ and $R_8$ are attached form a carbonyl;

$R_{10}$ is selected from the group consisting of
   (1) substituted or unsubstituted aryl,
   (2) halogen, and
   (3) $OR_{10a}$,
   wherein $R_{10a}$ is selected from the group consisting of
      (a) hydrogen,
      (b) substituted or unsubstituted alkyl, and
      (c) substituted or unsubstituted aryl; and $R_9$, $R_{11}$, and $R_{12}$ are selected from the group consisting of
   (1) hydrogen,
   (2) substituted or unsubstituted alkyl, and
   (3) halogen, wherein the term "substituted" refers to the replacement of hydrogen with a radical selected from a group consisting of hydroxyl, halo, alkoxy, cyano, sulfide, sulfonamido, oxo, carboxyl, alkyl, haloalkyl, alkylcarbonyl, aminocarbonyl, amino, and alkylamino.

2. A compound of claim 1, wherein substituted alkyl comprises aminoalkyl, alkylaminoalkyl, or sulfonamidoalkyl.

3. A compound of claim 1, wherein $R_1$ is hydrogen.

4. A compound of claim 1, wherein $R_2$ is phenyl or substituted phenyl.

5. A compound of claim 1, wherein $R_2$ is 3-hydroxyphenyl.

6. A compound of claim 1, wherein the nitrogen containing group is selected from the group consisting of aminomethyl, 2-aminoethyl, and 3-aminopropyl.

7. A compound of claim 1, wherein $R_5$, $R_6$, $R_7$, and $R_8$ are hydrogen.

8. A compound of claim 1, wherein $R_9$, $R_{11}$, and $R_{12}$ are hydrogen.

9. A compound of claim 1, wherein $R_{10}$ is selected from the group consisting of alkyl, alkoxy, aryl, halo, and hydroxy.

10. A compound selected from the group consisting of:
3-(6-chloro-2-glycyl-2,3,4,9-tetrahydro-1H-beta-carbolin-1-yl)phenol;
3-(2-beta-alanyl-6-methyl-2,3,4,9-tetrahydro-1H-beta-carbolin-1-yl)phenol;
3-[2-(4-aminobutanoyl)-6-methyl-2,3,4,9-tetrahydro-1H-beta-carbolin-1-yl]phenol;
3-(2-beta-alanyl-6-chloro-2,3,4,9-tetrahydro-1H-beta-carbolin-1-yl)phenol;
3-[6-chloro-2-(N,N-dimethyl-beta-alanyl)-2,3,4,9-tetrahydro-1H-beta-carbolin-1-yl] phenol;
3-{6-chloro-2-[4-(dimethylamino)butanoyl]-2,3,4,9-tetrahydro-1H-beta-carbolin-1-yl}phenol;
3-(6-bromo-2-glycyl-2,3,4,9-tetrahydro-1H-beta-carbolin-1-yl)phenol;
3-[2-(2-aminobutanoyl)-6-chloro-2,3,4,9-tetrahydro-1H-beta-carbolin-1-yl]phenol;
3-[2-(3-aminopropanoyl)-6-ethyl-2,3,4,9-tetrahydro-1H-beta-carbolin-1-yl]phenol;
3-[6-chloro-2-(piperidin-4-ylacetyl)-2,3,4,9-tetrahydro-1H-beta-carbolin-1-yl]phenol;
3-{6-bromo-2-[(dimethylamino)acetyl]-2,3,4,9-tetrahydro-1H-beta-carbolin-1-yl}phenol;
3-{6-bromo-2-[(methylamino)acetyl]-2,3,4,9-tetrahydro-1H-beta-carbolin-1-yl}phenol;
3-(2-beta-alanyl-8-methyl-2,3,4,9-tetrahydro-1H-beta-carbolin-1-yl)phenol; and
3-(2-beta-alanyl-7-fluoro-2,3,4,9-tetrahydro-1H-beta-carbolin-1-yl)phenol.

11. A composition, comprising a pharmaceutically acceptable carrier and an amount of a compound of any one of claim 1 or 10 effective to inhibit KSP activity in a human or animal subject when administered thereto.

* * * * *

UNITED STATES PATENT AND TRADEMARK OFFICE
CERTIFICATE OF CORRECTION

PATENT NO. : 7,855,295 B2
APPLICATION NO. : 11/042474
DATED : December 21, 2010
INVENTOR(S) : W. Wang et al.

It is certified that error appears in the above-identified patent and that said Letters Patent is hereby corrected as shown below:

| COLUMN | LINE | ERROR |
|---|---|---|
| 92 (Claim 9, | 6 line 2) | after "group consisting of" delete "alkyl" |
| 92 (Claim 11, | 39 line 2) | "claim 1 or 10" should read --claims 1 or 10-- |

Signed and Sealed this
Twenty-second Day of March, 2011

David J. Kappos
*Director of the United States Patent and Trademark Office*